US012758481B2

(12) United States Patent
Bader

(10) Patent No.: US 12,758,481 B2
(45) Date of Patent: Oct. 13, 2026

(54) COSMETIC FORMULATION FOR TOPICAL ADMINISTRATION COMPRISING NOVEL PEPTIDES THAT IMPROVE APPEARANCE AND REGENERATION OF SKIN

(71) Applicant: ASC REGENITY LTD., London (GB)

(72) Inventor: Augustinus Bader, Parthenstein (DE)

(73) Assignee: ASC REGENITY LTD, London (GB)

( * ) Notice: Subject to any disclaimer, the term of this patent is extended or adjusted under 35 U.S.C. 154(b) by 805 days.

(21) Appl. No.: 17/793,854

(22) PCT Filed: Jan. 18, 2021

(86) PCT No.: PCT/EP2021/025016
§ 371 (c)(1),
(2) Date: Jul. 19, 2022

(87) PCT Pub. No.: WO2021/148241
PCT Pub. Date: Jul. 29, 2021

(65) Prior Publication Data
US 2023/0135317 A1 May 4, 2023

(30) Foreign Application Priority Data
Jan. 21, 2020 (EP) .................................... 20000033

(51) Int. Cl.

| | |
|---|---|
| ***A61K 8/64*** | (2006.01) |
| ***A61K 8/11*** | (2006.01) |
| ***A61K 8/14*** | (2006.01) |
| ***A61K 8/81*** | (2006.01) |
| ***A61Q 19/00*** | (2006.01) |
| ***A61Q 19/08*** | (2006.01) |
| ***C07K 14/00*** | (2006.01) |

(52) U.S. Cl.
CPC .................. *A61K 8/64* (2013.01); *A61K 8/11* (2013.01); *A61K 8/14* (2013.01); *A61K 8/8111* (2013.01); *A61Q 19/007* (2013.01)

(58) Field of Classification Search
CPC ... A61K 8/11; A61K 8/14; A61K 8/64; A61K 8/8111; A61Q 19/007; A61Q 19/08; C07K 14/00
See application file for complete search history.

(56) References Cited

U.S. PATENT DOCUMENTS 6,703,491 B1 * 3/2004 Homburger ............ A01K 67/65 435/6.16
7,214,786 B2 * 5/2007 Kovalic ............. C12N 15/8273 536/23.6
8,932,839 B2 * 1/2015 Breuer ..................... C12N 9/88 435/166
9,029,636 B2 * 5/2015 Wu ...................... C07K 14/415 800/320.2
9,206,464 B2 * 12/2015 Veidal ...................... C12Q 1/37
10,456,346 B2 10/2019 Bader
11,091,523 B2 * 8/2021 Hinck .................... A61K 45/06
11,607,443 B2 * 3/2023 Combier ................. A61P 11/00
11,912,751 B2 * 2/2024 De Los Santos ............................ C07K 14/70521
2012/0245086 A1 9/2012 Chung et al.
2020/0000878 A1 * 1/2020 Combier ................. A61P 31/14

FOREIGN PATENT DOCUMENTS

KR 10-2009-0132911 A 12/2009
WO 2018/086732 A1 5/2018

OTHER PUBLICATIONS

Yampolsky et al., "The Exchangeability of Amino Acids in Proteins," Genetics, 2005, 170: 1459-1472. (Year: 2005).*
S. Dekoninck et al., "Stem cell dynamics, migration and plasticity during wound healing", Nature Cell Biology, vol. 21, Jan. 2019, pp. 18-24.
L. Crigler et al., Isolation of a mesenchymal cell population from murine dermis that contains progenitors of multiple cell lineages:, The FASEB Journal, vol. 21, Jul. 2007, pp. 2050-2063.
Q. Fan et al., "Bone marrow-derived keratinocytes are not detected in normal skin and only rarely detected in wounded skin in two different murine models", Experimental Hematology, 34(5), 2006, pp. 672-679.
C. Blanpain et al., "Plasticity of epithelial stem cells in tissue regeneration", Science, vol. 344, Issue 6189, Jun. 13, 2014.
K. Lau et al., "Exploring the role of stem cells in cutaneous wound healing", Experimental Dermatology, vol. 18, Jun. 2009, pp. 921-933.
M. Hu et al., "Mesenchymal Stromal Cells and Cutaneous Wound Healing: A Comprehensive REview of the Background, Roll, and Therapeutic Potential", Stem Cells International, vol. 2018, Article ID 6901983, May 20, 2018, pp. 1-13.
M. Soundararajan et al., "Fibroblasts and mesenchymal stem cells: Two sides of the same coin?", Jounral of Cellular Physiology, Feb. 2018, pp. 1-11.
R. Driskell et al., "Distinct fibroblast lineages determine dermal architecture in skin development and repair", Nature, vol. 507, Dec. 12, 2013, pp. 277-281.
C. Philippeos et al., "Spatial and Single-Cell Transcriptional Profiling Identifies Functionally Distinct Human Dermal Fibroblast Subpopulations", Journal of Investigative Dermatology, vol. 138, 2018, pp. 811-825.

(Continued)

*Primary Examiner* — Julie Ha
(74) *Attorney, Agent, or Firm* — Secant IP, P.L.L.C.

(57) ABSTRACT

A novel nature-derived and synthetic active peptide- or peptide-derived agents designed for the cosmetic treatment of human skin, as well as cosmetic formulations and compositions containing them are provided. The active agents are effective in restoring, promoting and maintaining a healthy skin. In particular, combinations or sets of skin effective agents include stem-cell factors that modulate the skin micromilieu and modulate skin stem cell behaviour, thereby effectively healing, regenerating and improving the state of aged or damaged skin.

13 Claims, 2 Drawing Sheets

Figure 1:
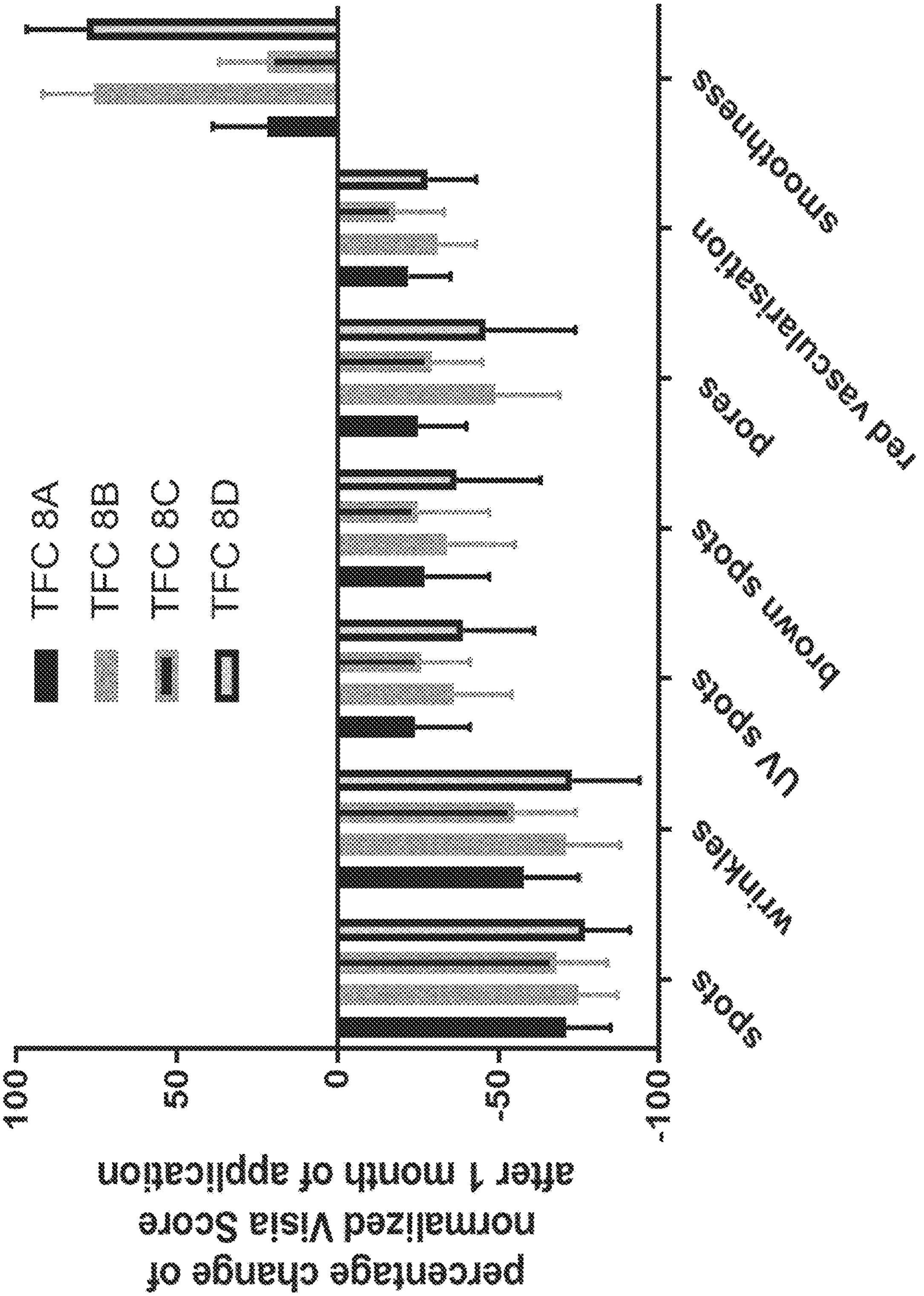

Specification includes a Sequence Listing.

(56) References Cited

OTHER PUBLICATIONS

C. Vaculik et al., "Human Dermis Harbors Distinct Mesenchymal Stromal Cell Subsets", Journal of Investigative Dermatology, vol. 132, Nov. 3, 2011, pp. 563-574.
M. Lynch et al., "Fibroblast heterogeneity: implications for human disease", The Journal of Clinical Investigation, vol. 128, No. 1, Jan. 2018, pp. 26-35.
D. Jiang et al., "Two succeeding fibroblastic lineages drive dermal development and the transition from regeneration to scarring", Nature Cell Biology, vol. 20, Apr. 2018, pp. 422-431.
Y. Rinkevich et al., "Identification and isolation of a dermal lineage with intrinsic fibrogenic potential", vol. 348, Issue 6232, Apr. 17, 2015.
M. Farage et al., "Textbook of Aging Skin", 2010, pp. 1-1220.
International Search Report Corresponding to PCT/EP2021/025016 mailed Apr. 28, 2021.
Written Opinion Corresponding to PCT/EP2021/025016 mailed Apr. 28, 2021.
U. Eckhard et al., "Active site specificity profiling of the matrix metalloproteinase family: Proteomic identification of 4300 cleavage sites by nine MMPs explored with structural and synthetic peptide cleavage analysis", Matrix Biology, 19(2016), pp. 37-60.
S. Ricard-Blum et al., "Matricryptins and matrikines: biologically active fragments of the extracellular matrix", Experimental Dermatology, 23(7), 2014, pp. 457-463.
E. Fisman et al., "Antidiabetic treatment with gliptins: focus on cardiovascular effects and outcomes", Cardiovascular Diabetology, 8(1), Sep. 29, 2015, pp. 24-28.
X. Lim et al., "Axin2 marks quiescent hair follicle bulge stem cells that are maintained by autocrine Wnt/β-catenin signaling", Proceedings of the National Academy of Sciences of the United States o America, 113(11), 2016, E1498-1505.
M. Mastrogiannaki et al., "β-Catenin Stabilization in Skin Fibroblasts Causes Fibrotic Lesions by Preventing Adipocyte Differentiation of the Reticular Dermis", Journal of Investigative Dermatology, vol. 136, 2016, pp. 1130-1142.
A. Attaway et al., "Bullous pemphigoid associated with dipeptidyl peptidase IV inhibitors. A case report and review of iterature.", Journal of Dermatological Case Reports, (8)1, 2014, pp. 24-28.
C. Marshall et al., "Cutaneous Scarring: Basic Science, Current Treatments, and Future Directions", Wound Healing Society, Advances in Wound Care, 7(2), 2016, pp. 1-17.
M. Leist et al., "Derivatives of Erythropoietin That Are Tissue Protective But Not Erythropoietic", Science, 305(5681), Jul. 9, 2004, pp. 239-424.
P. De Bona et al., "Design and synthesis of new trehalose-conjugated pentapeptides as inhibitors of Aβ(1-42) fibriollogenesis and toxicity", Journal of Peptide Science, 15(3), 2009, pp. 220-228.
S. Volk et al., "Diminished Type III Collagen Promotes Myofibroblast Differentiation and Increases Scar Deposition in Cutaneous Wound Healing", Cells Tissues Organs, 194(1), Jan. 19, 2011, pp. 25-37.
Y. Choi et al., "Distinct Functions for Wnt/β-Catenin in Hair Follicle Stem Cell Proliferation and Survival and Interfollicular Epidermal Homeostasis", Cell Stem Cell, 13(6), Dec. 5, 2013, pp. 720-733.
K. Nakatani et al., "Drug-Induced Generalized Skin Eruption in a Diabetes Mellitus Patient Receiving a Dipeptidyl Peptidase-4 Inhibitor Plus Metformin", Diabetes Therapy, 3(1), 2012, pp. 1-5.
G. Falck et al. "Enzyme-Based Labeling Strategies for Antibody-Drug Conjugates and Antibody Mimetics" Antibodies, (1), 4, Jan. 4, 2018, pp. 1-19.
B. Lichtenberger et al., "Epidermal β-catenin activation remodels the dermis via paracrine signalling to distinct fibroblast lineages", Nature Communications, 7, Feb. 3, 2016, pp. 1-13.
M. Xue et al., "Extracellular Matrix Reorganization During Wound Healing and Its Impact on Abnormal Scarring", Advances in Wound Care, 4(3), 2015, pp. 119-136.
M. Sternlicht et al., "How Matrix Metalloproteinases Regulate Cell Behavior", Annual Review of Cell and Developmental Biology, 17: 463-516, 2001.
X. Lim et al., "Interfollicular Epidermal Stem Cells Self-Renew via Autocrine Wnt Signaling", Science, 342(6163) Dec. 6, 2013, pp. 1226-1230.
H. Clevers et al., "An integral program for tissue renewal and regeneration: Wnt signaling and stem cell control", Science, vol. 346, Issue 6205, Oct. 3, 2014, 1248012.
V. Jaks et al., "Lgr5 marks cycling, yet long-lived, hair follicle stem cells", Nature Genetics, vol. 40, No. 11, Nov. 2008, pp. 1291-1299.
J. Wells et al., "MMP generated Matrikines", Matrix Biology, 44-46, 2015, pp. 122-129.
C.I. Günter et al., "New Strategies in Clinical Care of Skin Wound Healing", European Surgical Research, 49(1), Jul. 11, 2012, pp. 16-23.
T. Kamerzell et al., "Protein-excipeint interactions: Mechanisms and biophysical characterization applied to protein formulation development", Advanced Drug Delivery Reviews, 63(13), Jul. 29, 2011, pp. 1118-1159.
C. Bonnans et al., "Remodelling the extracellular matrix in development and disease", Nature Reviews Molecular Cell Biology, 15(12), Dec. 2014, pp. 786-801.
C. Collins et al., "Reprogramming adult dermis to a neonatal state through epidermal activation of β-catenin", Development, 138(23), Sep. 30, 2011, pp. 5189-5199.
D. Lo et al., "Scarless Fetal Skin Wound Healing Update", Review, Birth Defects Research (Part C), 96 (2012), pp. 237-247.
R. Gilbert et al., "Signalling by Transforming Growth Factor Beta Isoforms in Wound Healing and Tissue Regeneration", Journal of Developmental Biology, 4(21), Jun. 22, 2016, pp. 1-21.
C. Aldag et al., "Skin rejuvenation using cosmetic products containing growth factors, cytokines, and matrikines: a review of the literature", Clinical, Cosmetic and Investigational Dermatology, 9, Nov. 9, 2016, pp. 411-419.
C. Janda et al., "Surrogate Wnt agonists that phenocopy canonical Wnt and β-catenin signalling", Nature, 545(7653), May 11, 2017, pp. 234-437.
"Synthesis of 6-Amino-6-Deoxy-Trehalose: a Positional α,α-Isomer of Trehalosamine", The Journal of Antibiotics, vol. XXV, No. 11, Nov. 1972, pp. 683-684.
A. Dutta et al., "Trehalose Conjugation Enhances Toxicity of Photosensitizers against Mycobacteria", ACS Central Science, 5, Mar. 27, 2019, pp. 644-650.
A. Dutta et al., "Trehalose Conjugation Enhances Toxicity of Photosensitizers against Mycobacteria", ACS Central Science, 5, Mar. 27, 2019, pp. 644-650 (Supporting Information).
R. Mancini et al., "Trehalose Glycopolymers for Stabilization of Protein Conjugates to Environmental Stressors", Journal of the American Chemical Society, 134(20), Apr. 20, 2012, pp. 8474-8479.
R. Nusse et al., "Wnt/β-Catenin Signaling, Disease, and Emerging Therapeutic Modalities", Cell, 169, Jun. 16, 2017, pp. 985-999.
O. Burgy et al., "The WNT signaling pathways in wound healing and fibrosis", Matrix Biology, 68-69, Mar. 17, 2018, pp. 67-80.
M. Katoh, "WNT Signaling in Stem Cell Biology and Regenerative Medicine", Current Drug Targets, 9(7), 2008, pp. 565-570.

* cited by examiner

SEQUENCE LISTING

```
<160> NUMBER OF SEQ ID NOS: 19

<210> SEQ ID NO 1
<211> LENGTH: 34
<212> TYPE: PRT
<213> ORGANISM: Artificial Sequence
<220> FEATURE:
<223> OTHER INFORMATION: peptide that stimulates the Wnt beta-catenin
      signaling pathway

<400> SEQUENCE: 1

Leu Asn Pro Ser Glu Cys Pro Lys Thr Val Leu Gly Ala Glu Tyr Gly
1               5                   10                  15

Lys Thr Leu Asp Ala Ser Tyr Ser Thr Ala Glu Ala Glu Asn His Val
            20                  25                  30

Arg Leu


<210> SEQ ID NO 2
<211> LENGTH: 33
<212> TYPE: PRT
<213> ORGANISM: Artificial Sequence
<220> FEATURE:
<223> OTHER INFORMATION: peptide that stimulates the Wnt beta-catenin
      signaling pathway

<400> SEQUENCE: 2

Leu Asn Pro Ser Glu Cys Pro Lys Thr Val Leu Gly Ala Ser Thr Ser
1               5                   10                  15

Thr Leu Asp Ala Ser Tyr Ser Thr Ala Glu Ala Glu Asn His Val Arg
            20                  25                  30

Leu


<210> SEQ ID NO 3
<211> LENGTH: 35
<212> TYPE: PRT
<213> ORGANISM: Artificial Sequence
<220> FEATURE:
<223> OTHER INFORMATION: peptide that stimulates the Wnt beta catenin
      signaling pathway
<220> FEATURE:
<221> NAME/KEY: VARIANT
<222> LOCATION: 1
<223> OTHER INFORMATION: Xaa is any carrier moiety covalently attached
      to the N-terminus of said peptide that reduces skin penetration,
      such as polyethyleneglycol (PEG)

<400> SEQUENCE: 3
```

```
Xaa Leu Asn Pro Ser Glu Cys Pro Lys Thr Val Leu Gly Ala Glu Tyr
1               5                   10                  15

Gly Lys Thr Leu Asp Ala Ser Tyr Ser Thr Ala Glu Ala Glu Asn His
            20                  25                  30

Val Arg Leu
        35


<210> SEQ ID NO 4
<211> LENGTH: 34
<212> TYPE: PRT
<213> ORGANISM: Artificial Sequence
<220> FEATURE:
<223> OTHER INFORMATION: peptide that stimulates the Wnt beta-catenin
      signaling pathway
<220> FEATURE:
<221> NAME/KEY: VARIANT
<222> LOCATION: 1
<223> OTHER INFORMATION: Xaa is any carrier moiety covalently attached
      to the N-terminus of said peptide that reduces skin penetration,
      such as polyethyleneglycol (PEG)

<400> SEQUENCE: 4

Xaa Leu Asn Pro Ser Glu Cys Pro Lys Thr Val Leu Gly Ala Ser Thr
1               5                   10                  15

Ser Thr Leu Asp Ala Ser Tyr Ser Thr Ala Glu Ala Glu Asn His Val
            20                  25                  30

Arg Leu


<210> SEQ ID NO 5
<211> LENGTH: 22
<212> TYPE: PRT
<213> ORGANISM: Artificial Sequence
<220> FEATURE:
<223> OTHER INFORMATION: peptide agonist of tissue-protective
      heterodimeric or heterooligomeric EPOR/CD131 (erythropoietin
      receptor/cluster of differentiation 131) receptor

<400> SEQUENCE: 5

Gly Gly Gly Gly Glu Thr Thr Asn Met Trp Ala Arg Glu Trp Met Gly
1               5                   10                  15

Leu Pro Cys Gln Asp Gln
            20


<210> SEQ ID NO 6
<211> LENGTH: 23
<212> TYPE: PRT
<213> ORGANISM: Artificial Sequence
<220> FEATURE:
<223> OTHER INFORMATION: peptide agonist of tissue-protective
      heterodimeric or heterooligomeric EPOR/CD131 (erythropoietin
      receptor/cluster of differentiation 131) receptor
<220> FEATURE:
<221> NAME/KEY: VARIANT
<222> LOCATION: 1
<223> OTHER INFORMATION: Xaa is an acyl group of a branched or
      unbranched fatty acid of 5 - 42 carbon atoms covalently attached
      to the N-terminus of the peptide

<400> SEQUENCE: 6

Xaa Gly Gly Gly Gly Glu Thr Thr Asn Met Trp Ala Arg Glu Trp Met
1               5                   10                  15

Gly Leu Pro Cys Gln Asp Gln
            20


<210> SEQ ID NO 7
<211> LENGTH: 112
```

```
<212> TYPE: PRT
<213> ORGANISM: Artificial Sequence
<220> FEATURE:
<223> OTHER INFORMATION: peptide variant of human TGF-beta

<400> SEQUENCE: 7

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Lys His Ser Thr Val Leu Gly Leu
    50                  55                  60

Tyr Asn Thr His Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Glu Asn Met Val Val Lys Ser Cys Lys Cys Ser
            100                 105                 110


<210> SEQ ID NO 8
<211> LENGTH: 119
<212> TYPE: PRT
<213> ORGANISM: Artificial Sequence
<220> FEATURE:
<223> OTHER INFORMATION: peptide variant of human TGF-beta
<220> FEATURE:
<221> NAME/KEY: VARIANT
<222> LOCATION: 115
<223> OTHER INFORMATION: Xaa = Lys or Glu

<400> SEQUENCE: 8

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Lys His Ser Thr Val Leu Gly Leu
    50                  55                  60

Tyr Asn Thr His Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Glu Asn Met Val Val Lys Ser Cys Lys Cys Ser
            100                 105                 110

Leu Pro Xaa Thr Gly Gly Gly
        115


<210> SEQ ID NO 9
<211> LENGTH: 120
<212> TYPE: PRT
<213> ORGANISM: Artificial Sequence
<220> FEATURE:
<223> OTHER INFORMATION: peptide variant of human TGF-beta
<220> FEATURE:
<221> NAME/KEY: VARIANT
<222> LOCATION: 115
<223> OTHER INFORMATION: Xaa = Lys or Glu
<220> FEATURE:
<221> NAME/KEY: VARIANT
```

-continued

<222> LOCATION: 120
<223> OTHER INFORMATION: Xaa is a glycopolymer of 15 - 50 monomeric units attached to the C-terminus of the peptide

<400> SEQUENCE: 9

Ala Leu Asp Thr Asn Tyr Cys Phe Arg Asn Leu Glu Glu Asn Cys Cys
1 5 10 15

Val Arg Pro Leu Tyr Ile Asp Phe Arg Gln Asp Leu Gly Trp Lys Trp
20 25 30

Val His Glu Pro Lys Gly Tyr Tyr Ala Asn Phe Cys Ser Gly Pro Cys
35 40 45

Pro Tyr Leu Arg Ser Ala Asp Thr Lys His Ser Thr Val Leu Gly Leu
50 55 60

Tyr Asn Thr His Asn Pro Glu Ala Ser Ala Ser Pro Cys Cys Val Pro
65 70 75 80

Gln Asp Leu Glu Pro Leu Thr Ile Leu Tyr Tyr Val Gly Arg Thr Pro
85 90 95

Lys Val Glu Gln Leu Glu Asn Met Val Val Lys Ser Cys Lys Cys Ser
100 105 110

Leu Pro Xaa Thr Gly Gly Gly Xaa
115 120

<210> SEQ ID NO 10
<211> LENGTH: 23
<212> TYPE: PRT
<213> ORGANISM: Artificial Sequence
<220> FEATURE:
<223> OTHER INFORMATION: antagonist of the tissue-protective heterodimeric or heterooligomeric EPOR/CD131 (erythropoietin receptor/cluster of differentiation 131) receptor
<220> FEATURE:
<221> NAME/KEY: VARIANT
<222> LOCATION: 1
<223> OTHER INFORMATION: Xaa is an acyl group of a branched or an unbranched fatty acid of 5 - 42 carbon atoms attached to the N-terminus of the peptide

<400> SEQUENCE: 10

Xaa Gly Gly Gly Gly Glu Thr Thr Asn Met Trp Ala His Asp Trp Met
1 5 10 15

Gly Leu Pro Arg Ala Asp Gln
20

<210> SEQ ID NO 11
<211> LENGTH: 48
<212> TYPE: PRT
<213> ORGANISM: Artificial Sequence
<220> FEATURE:
<223> OTHER INFORMATION: peptide that elicits collagen type 3-derived matrikine activity

<400> SEQUENCE: 11

Leu Gln Gly Leu Pro Gly Thr Gly Gly Pro Pro Gly Glu Asn Gly Lys
1 5 10 15

Pro Gly Glu Pro Gly Pro Lys Gly Asp Ala Gly Ala Pro Gly Ala Pro
20 25 30

Gly Gly Lys Gly Asp Ala Gly Ala Pro Gly Glu Arg Gly Pro Pro Gly
35 40 45

<210> SEQ ID NO 12
<211> LENGTH: 24
<212> TYPE: PRT
<213> ORGANISM: Artificial Sequence

```
<220> FEATURE:
<223> OTHER INFORMATION: peptide that elicits collagen type 3-derived
      matrikine activity

<400> SEQUENCE: 12

Val Lys Gly Glu Ser Gly Lys Pro Gly Ala Asn Gly Leu Ser Gly Glu
1               5                   10                  15

Arg Gly Pro Pro Gly Pro Gln Gly
            20


<210> SEQ ID NO 13
<211> LENGTH: 49
<212> TYPE: PRT
<213> ORGANISM: Artificial Sequence
<220> FEATURE:
<223> OTHER INFORMATION: peptide or peptide that elicits collagen type
      3-derived matrikine activity
<220> FEATURE:
<221> NAME/KEY: VARIANT
<222> LOCATION: 1
<223> OTHER INFORMATION: Xaa is an acyl group of an unbranched or
      branched fatty acid of 5 - 42 carbon atoms

<400> SEQUENCE: 13

Xaa Leu Gln Gly Leu Pro Gly Thr Gly Gly Pro Pro Gly Glu Asn Gly
1               5                   10                  15

Lys Pro Gly Glu Pro Gly Pro Lys Gly Asp Ala Gly Ala Pro Gly Ala
            20                  25                  30

Pro Gly Gly Lys Gly Asp Ala Gly Ala Pro Gly Glu Arg Gly Pro Pro
        35                  40                  45

Gly


<210> SEQ ID NO 14
<211> LENGTH: 25
<212> TYPE: PRT
<213> ORGANISM: Artificial Sequence
<220> FEATURE:
<223> OTHER INFORMATION: peptide or peptide that elicits collagen type
      3-derived matrikine activity
<220> FEATURE:
<221> NAME/KEY: VARIANT
<222> LOCATION: 1
<223> OTHER INFORMATION: Xaa is an acyl group of an unbranched or
      branched faty acid of 5 - 42 carbon atoms

<400> SEQUENCE: 14

Xaa Val Lys Gly Glu Ser Gly Lys Pro Gly Ala Asn Gly Leu Ser Gly
1               5                   10                  15

Glu Arg Gly Pro Pro Gly Pro Gln Gly
            20                  25


<210> SEQ ID NO 15
<211> LENGTH: 19
<212> TYPE: PRT
<213> ORGANISM: Artificial Sequence
<220> FEATURE:
<223> OTHER INFORMATION: peptide that elicits CD26/Dpp4 inhibition
<220> FEATURE:
<221> NAME/KEY: VARIANT
<222> LOCATION: 16
<223> OTHER INFORMATION: Xaa is Gly and has an isopeptide bond via its
      carboxy group to the epsilon amino group of the neigbboured Lys on
      the C-terminal side
<220> FEATURE:
<221> NAME/KEY: VARIANT
<222> LOCATION: 17
<223> OTHER INFORMATION: Xaa is Lys and has an isopeptide bond via its
      epsilon amino group to the carboxy group of neigbboured Gly on the
```

N-terminal side

<400> SEQUENCE: 15

Glu Ile His Gln Glu Glu Pro Ile Gly Gly Gln Ser Gly Ser Gly Xaa
1 5 10 15

Xaa Pro Ile

<210> SEQ ID NO 16
<211> LENGTH: 19
<212> TYPE: PRT
<213> ORGANISM: Artificial Sequence
<220> FEATURE:
<223> OTHER INFORMATION: peptide that elicits CD26/Dpp4 inhibition
<220> FEATURE:
<221> NAME/KEY: VARIANT
<222> LOCATION: 11
<223> OTHER INFORMATION: Xaa is Lys wherein the (free) epsilon amino group is bonded to an acyl group of an unbranched or branched fatty acid of 5 - 42 carbon atoms
<220> FEATURE:
<221> NAME/KEY: VARIANT
<222> LOCATION: 16
<223> OTHER INFORMATION: Xaa = Gly, wherein Gly has an isopeptide bond via its carboxy group to the epsilon amino group of neighboured Lys at the C-terminal side
<220> FEATURE:
<221> NAME/KEY: VARIANT
<222> LOCATION: 17
<223> OTHER INFORMATION: Xaa = Lys, wherein Lys is bonded via its epsilon amino group to the carboxy group of neighboured Gly at N-terminal side (isopeptide bond)

<400> SEQUENCE: 16

Glu Ile His Gln Glu Glu Pro Ile Gly Gly Xaa Ser Gly Ser Gly Xaa
1 5 10 15

Xaa Pro Ile

<210> SEQ ID NO 17
<211> LENGTH: 22
<212> TYPE: PRT
<213> ORGANISM: Artificial Sequence
<220> FEATURE:
<223> OTHER INFORMATION: antagonist of the tissue-protective heterodimeric or heterooligomeric EPOR/CD131 (erythropoietin receptor/cluster of differentiation 131) receptor

<400> SEQUENCE: 17

Gly Gly Gly Gly Glu Thr Thr Asn Met Trp Ala His Asp Trp Met Gly
1 5 10 15

Leu Pro Arg Ala Asp Gln
20

<210> SEQ ID NO 18
<211> LENGTH: 120
<212> TYPE: PRT
<213> ORGANISM: Artificial Sequence
<220> FEATURE:
<223> OTHER INFORMATION: fusion protein bewteen a peptide variant of TGF-beta3 and one or more units of (modified) trehalose
<220> FEATURE:
<221> NAME/KEY: VARIANT
<222> LOCATION: 115
<223> OTHER INFORMATION: Xaa is Lys or Glu
<220> FEATURE:
<221> NAME/KEY: VARIANT
<222> LOCATION: 120
<223> OTHER INFORMATION: Xaa is -[4,6-O-(4-vinylbenzylidene)-a,a-D-trehalose]n, wherein n is an integer between 1 and 50, preferably 10 and 30

```
<400> SEQUENCE: 18

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Lys His Ser Thr Val Leu Gly Leu
    50                  55                  60

Tyr Asn Thr His Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Glu Asn Met Val Val Lys Ser Cys Lys Cys Ser
            100                 105                 110

Leu Pro Xaa Thr Gly Gly Gly Xaa
        115                 120


<210> SEQ ID NO 19
<211> LENGTH: 120
<212> TYPE: PRT
<213> ORGANISM: Artificial Sequence
<220> FEATURE:
<223> OTHER INFORMATION: fusion protein between a peptide variant of
      TGF-beta3 and one or more units of (modified) trehalose
<220> FEATURE:
<221> NAME/KEY: VARIANT
<222> LOCATION: 115
<223> OTHER INFORMATION: Xaa is Lys or Glu
<220> FEATURE:
<221> NAME/KEY: VARIANT
<222> LOCATION: 120
<223> OTHER INFORMATION: Xaa is one or mor units of -Q-6-deoxy-trehalose
      (Q-6doTh)n, wherein n is an integer between 1 and 50, preferably
      10 and 30

<400> SEQUENCE: 19

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Lys His Ser Thr Val Leu Gly Leu
    50                  55                  60

Tyr Asn Thr His Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Glu Asn Met Val Val Lys Ser Cys Lys Cys Ser
            100                 105                 110

Leu Pro Xaa Thr Gly Gly Gly Xaa
        115                 120
```

COSMETIC FORMULATION FOR TOPICAL ADMINISTRATION COMPRISING NOVEL PEPTIDES THAT IMPROVE APPEARANCE AND REGENERATION OF SKIN

REFERENCE TO AN ELECTRONIC SEQUENCE LISTING

The contents of the electronic sequence listing (HEUBENP38US-SEQ_LIST_FINAL3.txt; Size: 14,658 bytes; and Date of Creation: Jul. 19, 2022) is herein incorporated by reference in its entirety.

FIELD OF THE INVENTION

The invention relates to novel nature-derived and synthetic active peptide or peptide-derived agents designed for the cosmetic treatment of the human skin, as well to cosmetic formulations and compositions containing them. The active agents are effective in restoring, promoting and maintaining a healthy skin.

In particular, the invention discloses combinations or sets of said skin effective agents including stem-cell factors that trigger the repair und regeneration of skin cells, thus effectively healing and improving the state of aged or damaged skin by synergistic action or by mutual alleviation of unwanted effects. These novel sets of agents and factors are designated according to the invention as "trigger factor complexes".

BACKGROUND OF THE INVENTION

Skin Homeostasis and Wound Healing

The human skin is one of the body's main barriers to the outside world and is constantly exposed to damaging insults. To prevent a constant deprecation of the skin state, biology has developed various regenerative mechanisms. In the homeostatic state a constant turnover of cells in the skin epithelium entails a shedding of old cells at the surface and a compensatory generation of new cells to replace the lost. Upon more severe insults such as trauma (wounds), irradiation, chemical damage or inflammation an accumulation of damage cues in the skin lead to a mounting of sophisticated innate repair programmes. In both homeostatic cell turnover and dedicated repair programmes, stem cells and progenitor cells act as key executors of skin maintenance. In both cases, they ultimately provide the new cells to replace the old and lost cells. Typically, dedicated repair programmes follow four phases: (I) haemostasis (in case of open wounds), (II) inflammation, (III) proliferation and (IV) tissue remodelling. Both processes, homeostatic cell turnover and dedicated repair programmes, including their sub-phases, have to be tightly regulated. For instance, misregulation of cell proliferation by failing to limit the generation of new cells both in homeostasis and in dedicated repair programmes can result in cancer initiation. Conversely, failure to provide enough new cells slows the regeneration process and compromise the skin's barrier function. Likewise, failure to limit or shut down inflammation can result in chronic inflammatory diseases, local tissue degeneration, stem cell pool exhaustion or autoimmune diseases. Conversely, failure to mount an appropriately profound inflammatory response to the damaging insult leads to failure in exercising the full regenerative capabilities equally compromising the skin's barrier function and risking opportunistic infections. At the tissue remodelling level, failure to mount this phase leaves the skin with temporary tissue with compromised functionality such as missing skin appendages and sub-optimal extracellular matrix composition. Conversely, failure to terminate the tissue remodelling phase equally results in incorrect extracellular matrix compositions and may contribute to fibrosis. Therefore, the body has developed sophisticated mechanisms to orchestrate the orderly execution of the skin maintenance and repair programmes. However, additional complexity is due to the fact that tissue regeneration not always is a linear path with a sequence of pre-determined steps. When the innate repair mechanisms are overwhelmed, e.g. by very large wounds, aging, or constant insults and associated exhaustion of regenerative capabilities, functional repair is compromised and a 'damage-control' programme ultimately entailing scarring is mounted.

Stem Cells

Stem cells and progenitor cells contribute to skin healing by providing new cells. Different stem cell populations give rise functional skin cells depending on the skin compartment. The epidermis is the outermost layer of the skin and both cell turnover in homeostasis and re-epithelialisation upon wounding is mediated by mostly epidermis-resident stem cells. The bulk of the epidermis surface is covered by the inter-follicular epithelium (IFE); other epithelial structures of skin epithelium include the hair follicles and sweat glands. Different stem cell and progenitor cell populations reside in own niches within the skin epithelium: stem cells (Itg2$\alpha^{high}$, Itg1$\alpha^{high}$) in the IFE, progenitors (Inv$^+$, Lgr6$^+$) in the IFE, stem cells (Lrig1$^+$) in the Infundibulum, stem cells (Gata6$^+$) in sebaceous gland ducts, stem cells (Lrig1$^+$, Lgr6$^+$, Blimp1$^+$, Plet1$^+$) in the isthmi and sebaceous glands, and stem cells (K15$^+$, K19$^+$, Lgr5$^+$, CD34$^+$, Sox9$^+$, Tcf3$^+$) in the bulge (Dekoninck & Blanpain, 2019, *Nature Cell Biology,* 21 (1), 18-24.). All these cells can contribute to temporary IFE epithelium cell replenishment in wounds. Moreover, both skin-resident mesenchymal stem cells (MSC) (Crigler et al., 2007, *The FASEB Journal,* 21 (9), 2050-2063) and hematopoietic stem cells (HSC) (Fan et al., 2006, *Experimental Hematology,* 34 (5), 672-679) can additionally contribute to epithelial regeneration to some extent. However, among all these sources the IFE stem cells and progenitors are the biggest epithelial cell contributors of both short-term and long-term repair upon wounding (Blanpain & Fuchs, 2014, *Science,* 344 (6189)). MSC have been reported to reside in defined niches of the dermal papilla (DP) and the connective tissue sheath (CTS) of the hair follicle (Lau, Paus, Tiede, Day, & Bayat, 2009, *Experimental Dermatology,* 18 (11), 921-933). Moreover, dermal and epidermal compartment are not isolated from one another, but rather communicate and co-operate. For instance, MSC engage in a paracrine secretion loop with keratinocytes and their precursor cells, thereby stimulating re-epithelialisation (Lau et al., 2009).

Mesenchymal stem cells (MSC) are key players in skin homeostasis, cell turnover, ECM dynamics and tissue regeneration. MSC replenish the mesenchymal cell pool, engage in ECM protein deposition and degradation, and regulate tissue dynamics by secretion of growth factors and cytokines. Various subclasses of MSC reside in different niches in the skin (Hu, Borrelli, Lorenz, Longaker, & Wan, 2018, *Stem Cells International,* 2018, 1-13.). These encompass hair follicle (HF)-resident cells such as dermal sheath cells and dermal papilla cells, interfollicular MSC in the dermis, vasculature-associated pericytes and adipose-derived MSC in the hypodermis. Moreover contribution of predominantly bone marrow-derived MSC infiltrating from the vasculature into the skin has been reported. Stem cells are generally defined by the ability to self-renew and to differentiate into functional cell types. As regular fibroblasts are morphologically indistinguishable from MSC and formally fulfil the defining criteria of (multipotent) stem cells, the past distinction of MSC/fibroblasts relating to stem cell status is under debate (Soundararajan & Kannan, 2018, *Journal of Cellular Physiology. Wiley-Liss Inc*, December 1). Regardless of that formal classification, the role of fibroblasts in skin homeostasis, ECM dynamics and wound healing is well established (Rognoni & Watt, 2018, *Trends in Cell Biology,* 28 (9), 709-722). Nevertheless, mesenchymal phenotypical diversity is further elaborated by dermal layer-associated lineages such as papillary (upper dermal) and reticular (lower dermal) fibroblasts (Driskell et al., 2013, *Nature,* 504 (7479), 277-281). The papillary lineage has 'pro-regeneration' phenotype and is required for the formation of hair follicles, whereas the reticular lineage is required for quick wound closure but also contributes to fibrosis-associated ECM deposition in a 'pro-scarring' manner. Mesenchymal cell heterogeneity has also been studied on molecular level (Philippeos et al., 2018, *Journal of Investigative Dermatology,* 138 (4), 811-825; Vaculik et al., 2012, *Journal of Investigative Dermatology,* 132 (3 PART 1), 563-574) and more detailed lineage relationships have been reviewed recently (Lynch & Watt, 2018).

Moreover, additional to microenvironment (dermal layer)-associated phenotypic diversity in mesenchymal cells, cell-intrinsic heterogeneity also exists and is a dominant determinant of regenerative behaviour. One major factor is Engrailed-1 (En-1) status (Jiang et al., 2018, *Nature Cell Biology,* 20 (4), 422-431; Rinkevich et al., 2015, *Science,* 348 (6232)). En-1-negative fibroblasts (ENF) mediate scarless wound healing during embryonic development. However, ENF numbers decline after embryonic development and En-1-positive fibroblasts (EPF) emerge as dominant lineage and promote scar formation.

Attributes of Ageing Skin

In aging skin, cell replacement is continuously declining, the barrier function and mechanical protection are compromised, wound healing and immune responses are delayed, thermoregulation is impaired, and sweat and sebum production are decreased (Farage, Miller, & Maibach, 2010, *Textbook of Aging Skin,* 1-1220). The reduced cell turnover rate results in roughness, delayed wound healing and uneven pigmentation. Elderly people more often suffer from dry skin than young, healthy individuals. This is based on a reduced function of sebaceous glands in producing natural moisturizing factors and lipids in the stratum corneum, thereby leading to decreased lamellar bilayers and poorer water-holding capacity. The aging of the skin is also accompanied by an extensive remodelling of extracellular matrix (ECM) in dermal layers, senescence of skin fibroblasts, dramatic upregulation of matrix metalloproteinases (MMPs), and a decrease of collagen production. Consequential general shortage and fragmentation of collagen, elastic fibers and other ECM protein leads to a loss of tensile strength manifesting as wrinkles and lax skin. Moreover, a flattening of the dermal papillae results in a greater risk of blister formation and consequent infection.

Impaired Skin Regeneration and Scarring Correlates with Signaling Molecule Patterns Biological processes are regulated on various levels, including the cellular and molecular level. Cells, including stem cells, integrate internal states and external cues for biological decision-making. Likewise, physiological skin homeostasis and regeneration is governed by defined sets of signalling molecules acting in defined times in defined places.

Enhancing Skin Regeneration by Trigger Factors

Despite its ability to maintain a functional skin for most part, the body's homeostasis and self-repair mechanisms are not perfect. This can be exacerbated, for instance by the occurrence of very large wounds, chronic activation-triggered exhaustion of the repair capabilities, aging, epigenetic deprecation, or another acute or chronic disease or stress factor.

However, the shortcomings of the innate regulatory systems can be alleviated or even overcome by external modulation. When functional recovery is the aim, external modulation typically requires an approach to overcome a regulatory deadlock. In turn, this often stipulates a multipronged approach targeting multiple regulatory hubs. However, conventional interventions often comprise a "one-entity-one-target" strategy and thus possess limited efficacy. Moreover, short term improvements often do not correlate with an overcoming of the regulatory deadlock, thereby leading to a persistent reliance on the short-term modulation. For instance, anti-inflammatory drugs provide great short-term relief by limiting inflammation without overcoming the regulatory deadlock or allowing functional recovery. Thus the inflammation often re-surges once the drug is withdrawn.

Previous efforts trying to harness the regenerative capacity of stem cells relying on supplying external stem cells from various sources to the skin have exhibited limited success. EPOR-CD131 agonist peptide-lipid complexes and conjugates have initially presented elegant alternatives when used in conjunction with vasorelaxant agents (International Patent Application WO 2018/086732, U.S. Pat. No. 10,456,346). These agents proved beneficial in cosmetic formulations in the short term application but turned out to be less favourable or even harmful during prolonged administration.

SUMMARY OF THE INVENTION

In a first aspect, the invention relates to single novel peptide- or peptide derived agents which are separately or in combination effective in regeneration and maintaining of the human skin. These agents are characterized by the peptide sequences/formulas presented by SEQ ID NOs: 1-19, described in more detail in the following sections.

In a second aspect, the invention relates to a cosmetic formulation or composition for topical administration to the skin comprising at least one peptide or peptide derivative which triggers or enhances or improves regeneration or appearance of skin, wherein the at least one peptide or peptide derivative is selected from the group (A) consisting of peptides and peptide derivatives that stimulate the Wnt/β-catenin signaling pathway and comprise or have the sequence/formula:

```
                                      (SEQ ID NO: 1)
(i)     LNPSECPKTVLGAEYGKTLDASYSTAEAENHVRL

                                      (SEQ ID NO: 2)
(ii)    LNPSECPKTVLGASTSTLDASYSTAEAENHVRL

                                      (SEQ ID NO: 3)
(iii)   Z1-LNPSECPKTVLGAEYGKTLDASYSTAEAENHVRL

                                      (SEQ ID NO: 4)
(iv)    Z1-LNPSECPKTVLGASTSTLDASYSTAEAENHVRL
```

wherein Z1 is a carrier moiety covalently attached to the N-terminus of said peptide that reduces tissue penetration and/or basal membrane transpermeation of said peptide.

In a preferred embodiment of the invention, Z1 is a polyethylene glycol (PEG) having a molecular weight in a range of 8-60 kDa, preferably 20-40 kDa.

In a third aspect, the invention relates to a cosmetic formulation or composition for topical administration to the skin comprising at least one peptide or peptide derivative which triggers or enhances or improves regeneration or appearance of skin, wherein at least one peptide or peptide derivative is selected from the group (B) consisting of peptides and peptide derivatives that are agonists of the tissue-protective heterodimeric or heterooligomeric EPOR/CD131 (erythropoietin receptor/cluster of differentiation 131) receptor, and comprise or have the sequence/formula:

(SEQ ID NO: 5)
(v) GGGGETTNMWAREWMGLPCQDQ (SEQ ID NO: 6)
(vi) Z2-GGGGETTNMWAREWMGLPCQDQ wherein Z2 is an acyl group of a branched or unbranched fatty acid covalently attached to the N-terminus of said peptide.

In a preferred embodiment of the invention, Z2 is a branched or an unbranched fatty acid of 5-42 carbon atoms, preferably 5-25 carbon atoms, for example Z2 is myristolyl.

In a further preferred embodiment of the invention said peptide/peptide derivative-based agonist presented by SEQ ID NOs 5 or 6 is partially or fully inactivated during application, preferably by air oxidation of a methionine residue within the peptide sequence.

In a further preferred embodiment of the invention the cosmetic formulation or composition further comprises an adequate amount of a peptide/peptide derivative-based antagonist of the tissue-protective heterodimeric or heterooligomeric EPOR/CD131 (erythropoietin receptor/cluster of differentiation 131) receptor, wherein said antagonist modulates or dampens or inhibits the biological activity of the agonist presented by SEQ ID NOs 5 or 6.

In a preferred embodiment of the invention said antagonist comprises or has the sequence/formula (SEQ ID NO: 17)
GGGGETTNMWAHDWMGLPRADQ
or (SEQ ID NO: 10)
Z2 - GGGGETTNMWAHDWMGLPRADQ wherein Z2 is an acyl group of a branched or an unbranched fatty acid of 5-42 carbon atoms, attached to the N-terminus of said peptide.

In a further preferred embodiment of the invention, said peptide/peptide derivative-based antagonist presented by SEQ ID NOs 10 or 17 is partially or fully inactivated during application, preferably by air oxidation of a methionine residue within the peptide sequence.

The modulation of activity of said EPOR/CD131 agonists and/or antagonists by oxidation by air oxygen of methionine residues in the sequences of said agents is a further important finding of the invention.

In a fourth aspect, the invention relates to a cosmetic formulation or composition for topical administration to the skin comprising at least one peptide or peptide derivative which triggers or enhances or improves regeneration or appearance of skin, wherein the at least one peptide or peptide derivative is selected from the group (C) consisting of peptides and peptide derivatives that are variants of human TGF-β3 and comprise or have the sequence/formula (SEQ ID NO: 7)
(vii) ALDTNYCFRNLEENCCVRPLYIDFRQDLGWKWVHEPKGYYANF
CSGPCPYLRSADTKHSTVLGLYNTHNPEASASPCCVPQDLEPL
TILYYVGRTPKVEQLENMVVKSCKCS (SEQ ID NO: 8)
(viii) ALDTNYCFRNLEENCCVRPLYIDFRQDLGWKWVHEPKGYYANF
CSGPCPYLRSADTKHSTVLGLYNTHNPEASASPCCVPQDLEPL
TILYYVGRTPKVEQLENMVVKSCKCSLPXTGGG (SEQ ID NO: 9)
(ix) ALDTNYCFRNLEENCCVRPLYIDFRQDLGWKWVHEPKGYYANF
CSGPCPYLRSADTKHSTVLGLYNTHNPEASASPCCVPQDLEPL
TILYYVGRTPKVEQLENMVVKSCKCSLPXTGGG-Z3 wherein X is K or E, and Z3 is a glycopolymer attached to the C-terminus.

In a preferred embodiment of the invention, Z3 is or comprises an oligomer or multimer or polymer comprising 15 to 50 monomeric units, preferably 18 to 30, containing moieties of trehalose or trehalose derivatives.

It could be shown here that trehalose derivative monomer units such as 4,6-O-(4-vinylbenzylidene)-α, α-D-trehalose or Q-6-deoxy-trehalose (Q-6doTh) are preferably suitable according to this invention. The attachment of Z3 at the C-terminus of the TGF-33 peptide sequences SEQ ID Nos. 7 and 8, resulting in the peptide derivative of SEQ ID NO: 9, causes more long-term stability of the resulting fusion molecules which is important for cosmetic formulations and respective application to skin.

Thus, the TGF-β3 fusion peptides, (SEQ ID NO: 18)
ALDTNYCFRNLEENCCVRPLYIDFRQDLGWKWVHEPKGYYANFCSGPCPY
LRSADTKHSTVLGLYNTHNPEASASPCCVPQDLEPLTILYYVGRTPKVEQ
LENMVVKSCKCSLPXTGGG-[4,6-O-(4-vinylbenzylidene)-α,
α-D-trehalose]$_n$,
and (SEQ ID NO: 19)
ALDTNYCFRNLEENCCVRPLYIDFRQDLGWKWVHEPKGYYANFCSGPCPY
LRSADTKHSTVLGLYNTHNPEASASPCCVPQDLEPLTILYYVGRTPKVEQ
LENMVVKSCKCSLPXTGGG-[Q-6doTh]$_n$, wherein X is K or E, and n is an integer between 15-50. represent specifically preferred embodiments of the invention.

The peptides or peptide derivatives as specified by any of the SEQ ID NOs: 1-19, may be optionally encapsulated into or attached to a liposome or ceramide structure for improving release properties during application.

It should be emphasized that each of the peptides mentioned above may be solely effective in the cosmetic treatment of skin described in more detail above and below.

Nonetheless, it could be shown by the inventors of this invention that combinations of two or three peptides each selected from the different groups (A), (B) and (C) as specified above and below, forming a so-called trigger factor complex for cosmetic skin applications, is much more effective and shows synergistic results with respect to skin therapeutic efficacy and long-term stability of the cosmetic formulations as compared to formulations containing the respective single agents only.

Therefore, in a fifth and important key aspect, the invention provides a set or trigger factor complex of said agents for use in topical cosmetic applications of skin comprising at least one peptide or peptide derivative of any of the groups (A) (B) (C) mentioned above and below, and at least one peptide or peptide derivative of a different group.

In other words, the invention provides (I) a first trigger factor complex comprising one or more peptide or peptide derivatives of group (A) and one or more peptide or peptide derivatives of group (B);

(II) a second trigger factor complex comprising one or more peptide or peptide derivatives of group (A) and one or more peptide or peptide derivatives of group (C);

(III) a third trigger factor complex comprising one or more peptide or peptide derivatives of group (B) and one or more peptide or peptide derivatives of group (C); and (IV) a fourth trigger factor complex comprising one or more peptide or peptide derivatives of group (A) and one or more peptide or peptide derivatives of group (B) and one or more peptide or peptide derivatives of group (C).

Each of the trigger factor complexes shows improved skin therapeutic properties compared to respective cosmetic formulations or compositions comprising a single peptide component from any of the groups (A) or (B) or (C) only.

Most effective, however, and therefore preferred according to the invention, is the trigger factor complex (IV) comprising at least one peptide or peptide derivative of group (A) and at least one peptide or peptide derivative of group (B), and at least one peptide or peptide derivative of group (C).

In more detail, a trigger factor complex is preferred, comprising (i) one or more peptide or peptide derivatives selected from group (A) consisting of:

(SEQ ID NO: 1)
LNPSECPKTVLGAEYGKTLDASYSTAEAENHVRL, (SEQ ID NO: 2)
LNPSECPKTVLGASTSTLDASYSTAEAENHVRL, (SEQ ID NO: 3)
Z1-LNPSECPKTVLGAEYGKTLDASYSTAEAENHVRL, (SEQ ID NO: 4)
Z1-LNPSECPKTVLGASTSTLDASYSTAEAENHVRL, and (ii) one or more peptide or peptide derivatives selected from group (A) consisting of:

(SEQ ID NO: 5)
GGGGETTNMWAREWMGLPCQDQ (SEQ ID NO: 6)
Z2-GGGGETTNMWAREWMGLPCQDQ, and (iii) one or more peptide or peptide derivatives selected from group (A) consisting of:

(SEQ ID NO: 7)
ALDTNYCFRNLEENCCVRPLYIDFRQDLGWKWVHEPKGYYANFCSGPCPY

-continued

LRSADTKHSTVLGLYNTHNPEASASPCCVPQDLEPLTILYYVGRTPKVEQ

LENMVVKSCKCS, (SEQ ID NO: 8)
ALDTNYCFRNLEENCCVRPLYIDFRQDLGWKWVHEPKGYYANFCSGPCPY

LRSADTKHSTVLGLYNTHNPEASASPCCVPQDLEPLTILYYVGRTPKVEQ

LENMVVKSCKCSLPXTGGG, (SEQ ID NO: 9)
ALDTNYCFRNLEENCCVRPLYIDFRQDLGWKWVHEPKGYYANFCSGPCPY

LRSADTKHSTVLGLYNTHNPEASASPCCVPQDLEPLTILYYVGRTPKVEQ

LENMVVKSCKCSLPXTGGG-Z3, wherein Z1, Z2, Z3 and X have the meanings as stated above.

Furthermore, the mentioned trigger factor complexes as well as the compositions comprising a single peptide or peptide derivative of any of the groups (A) (B) or (C) only, may comprise further agents and/or ingredients which are effective in cosmetic and skin therapeutic applications.

Thus, it has been shown by the inventors that-apart from the optional presence of the antagonists having the SEQ ID Nos 10 and 17, as disclosed above—a respective cosmetic formulation according to the invention may further comprise:

(a) a peptide or peptide derivative that elicits collagen type 3-derived matrikine activity and comprising or having one of the sequences/formulas selected from the group consisting of:

(SEQ ID NO: 11)
LQGLPGTGGPPGENGKPGEPGPKGDAGAPGAPGGKGDAGAPGERGPPG, (SEQ ID NO: 12)
VKGESGKPGANGLSGERGPPGPQG, (SEQ ID NO: 13)
Z2-LQGLPGTGGPPGENGKPGEPGPKGDAGAPGAPGGKGDAGAPGERGPP

G, (SEQ ID NO: 14)
Z2-VKGESGKPGANGLSGERGPPGPQG, and/or (b) a peptide or peptide derivative that elicits CD26/Dpp4 inhibition and comprises or has one of the sequences/formulas selected from the group consisting of:

(SEQ ID NO: 15)
EIHQEEPIGGQSGSGG-KPI, (SEQ ID NO: 16)
EIHQEEPIGGK[Z2]SGSGG-KPI, wherein Z2 is an acyl group of an unbranched or branched fatty acid of 5-42 carbon atoms, such as myristolyl, G-K denotes an isopeptide bond between the carboxy group of G (glycine) and the epsilon amino group of K (lysin), and K [Z2] denotes an amide bond between the epsilon amino function of K and the carboxy function of a fatty acid Z2 (such as myristolyl), has favourable and improved properties.

Taken together, and under consideration of the assumed general mode of action which shall be expressively regarded as not being binding with respect to the findings of this invention, the following can be stated:

This invention provides not only specific single peptide agents but also novel trigger factor complexes, i.e. some sets of novel peptide and/or chemical entities, that enable the body to harness its innate regenerative capabilities to a greater potential by overcoming multiple regulatory deadlocks.

The first key feature of the trigger factor complexes according to the invention is the suitability for a variety of insults and skin conditions entailing a broad application spectrum.

The second key feature of the trigger factor complexes of the invention is that all its components can be applied together in one formulation rather than sequentially in both time and space as the healing process would stipulate it for a one-agent modulation. This is the case, because the regulatory modulation exerted by the trigger factor complex co-operates with the local micro-environment. As a result, the activity of a given subset of the trigger factor complex is only effective when it is timely. For instance, the efficacy a given subset of the trigger factor complex is required at a given intermediate stage of the healing process. This subset of molecules of the trigger factor complex is always active, i.e. before its efficacy is required, when this is the case, and even after its efficacy is required. However, the trigger factor complex harnesses four mechanisms that govern the translation of activity into efficacy. First, this includes extracellular and intracellular signal transduction co-operation and modulation with local timing-specific skin state cues, including growth factors, cytokines, chemokines, damage-associated molecular patterns, neuronally-released molecules, ECM-molecules and matrikines. Second, this includes cell competence, i.e. receptiveness, to the applied trigger factor complex, for instance through cell surface receptor expression. Third, this includes harnessing the situational cellular responses to the same stimulation depending on the cells state. This particularly relates to the epigenetic state correlating to stem cell and progenitor cell differentiation states which in turn both correlate with the micromilieu in space and time. Fourth, the local micromilieu of protease activity, pH and oxidative potential regulates the local availability and activity of active ingredients.

The third key feature of the trigger factor complex is non-interference in absence of the insult. This means that the subset of the trigger factor complex that combats skin a condition “A”, does not cause adverse effects when applied to a skin affected by a condition “B” or healthy skin.

Furthermore, the trigger factor complexes according to the invention harness innate signaling pathways to drive cellular behavior. The molecules of the trigger factor complexes of the invention steer stem cell behaviour towards regenerative cellular programmes. This is achieved by modulating innate cellular signalling pathways that generally determine cellular behaviour.

Finally, the invention relates to the use of said cosmetic formulations and isolated peptide or peptide derivatives for the topical cosmetic treatment of human skin, including skin repair, rejuvenation of skin, natural skin glow, reduction of wrinkles, anti-aging of skin, and avoidance and improvement of dry, dull and rupture-prone skin.

DETAILED DESCRIPTION OF THE INVENTION

The term “peptide” means according to this invention any peptide having an amino acid sequence covalently linked together by amide bonds and the term “peptide” includes expressively peptides designated otherwise as polypeptides.

The term “peptide derivative” means according to this invention any chemical molecule that comprises a peptide moiety comprising at least five amino acids covalently linked together by amide bonds, wherein said peptide is covalently linked to a non-peptide moiety. Such non-peptide moiety expressively includes organic chemical residues such as but not limited to aliphatic, aromatic, homocyclic, heterocyclic, oligomeric or polymeric moieties. In particular said non-peptide moieties include fatty acids, trehalose or trehalose-derivative containing oligomers/polymers, and conventional pharmaceutical carriers such as polyethyleneglycol.

The term “Wnt/β-catenin signaling pathway” as used herein, means the Wnt pathway that causes an accumulation of β-catenin in the cytoplasm and its eventual translocation into the nucleus to act as a transcriptional coactivator of transcription factors that belong to the TCF/LEF family.

The term “EPOR/CD131 (erythropoietin receptor/cluster of differentiation 131) receptor as used herein, means the tissue-protective EPO receptor, comprising one or more EPO receptor subunits (EPOR) and one or more cluster of differentiation 131 proteins (CD131). The cluster of differentiation 131 protein is also known as cytokine receptor common subunit β (CSF2RB) or interleukin-3 receptor common β subunit (IL3RB).

The term “matrikines” as used herein, means peptides that originate from the fragmentation of extracellular matrix (ECM) proteins and regulate cellular activities by interacting with specific receptors. In the context of this invention, said matrikines include peptides which stimulate and modulate tissue regeneration and synthesis of extracellular matrix materials in skin tissue.

The term “trigger factor complex” as used herein, means a set of peptides, peptide derivatives and/or other chemical entities that enable the human skin to harness its innate regenerative capabilities to a greater extent by modulating the skin micromilieu and modulating stem cell behaviour.

Amino acid code: for disclosure of peptide sequences, the conventional one letter amino acid code is used herein. For clarity, A denotes alanine, C cysteine, D aspartic acid, E glutamic acid, F phenylalanine, G glycine, H histidine, I isoleucine, K lysine, L leucine, M methionine, N asparagine, P proline, Q glutamine, R arginine, S serine, T threonine, V valine, W tryptophan, Y tyrosine.

TGF Beta 3 Module

TGF beta signalling is a master regulator of skin homeostasis and regeneration (Gilbert, Vickaryous, & Viloria-Petit, 2016). All TGF beta isoforms (TGF beta 1, TGF beta 2, TGF beta 3) play crucial roles in wound healing. In simple terms, however, the different isoforms act as natural counterparts. TGF beta 1 and 2 promote the migration and activation of inflammatory cells, granulation tissue formation and fibroblast to myofibroblast transition, thereby promoting scar formation. By contrast, TGF beta 3 attenuates inflammatory processes, damage-associated ECM remodelling and limits the myofibroblast phenotype. Moreover, TGF beta 3's application is not limited to macro-injuries of the skin, but also steers cellular behaviour towards pro-regeneration in micro-injured or environmentally stressed skin. Nonetheless, TGF beta action in vivo is complex and administering recombinant TGF beta 3 provides no lasting therapeutic benefit as it was indicated by the failure of a clinical phase III study of the TGF beta 3 drug Juvista (Günter & MacHens, 2012, *European Surgical Research,* 49 (1), 16-23).

However, this invention discloses an engineered human TGF β variant, namely TGF β3 T57K L68H S102E, as suitable agent to support healthy skin for cosmetic applications. This construct can be produced recombinantly, e.g. from stably expressing CHO cells, and has the amino acid sequence:

(SEQ ID NO: 7)
ALDTNYCFRNLEENCCVRPLYIDFRQDLGWKWVHEPKGYYANFCSGPCPY

LRSADTKHSTVLGLYNTHNPEASASPCCVPQDLEPLTILYYVGRTPKVEQ

LENMVVKSCKCS.

Protein stability is a frequent issue for protein-based products. Many degradation pathways including chemical reactions, unfolding and aggregation contribute to loss of activity and generation of potentially harmful by-products such as immunogenic species like oligomers and higher-order assemblies. Intended use of proteins in biochemically complex mixtures such as cosmetic products poses an even greater challenge to ensure stability. Chemical species commonly used in cosmetic products including lipids thermodynamically favour the unfolded protein state exposing hydrophobic surfaces. Moreover, cosmetic products are rich in seeds for protein aggregation. In fact, recombinant TGF β3 T57K L68H S012E from mammalian expression hosts is not stable in standard cosmetic formulations for commercially compatible times. Recombinant proteins are often stabilized by excipients (Kamerzell, Esfandiary, Joshi, Middaugh, & Volkin, 2011, *Advanced Drug Delivery Reviews,* 63 (13), 1118-1159). However, many of these excipients interfere with the cosmetic formulation at effective protein-stabilizing concentrations or interact negatively with other cosmetic ingredients. Another elegant approach to protein stabilisation is post-purification glycopolymer-conjugation independent or additional to expression-related protein glycosylation (Mancini, Lee, & Maynard, 2012, *Journal of the American Chemical Society,* 134 (20), 8474-8479).

However, thiol-reactive conjugation is cysteine site-unspecific, thereby leading to labelling polymorphisms and moreover to labelling-induced non-functional TGF beta species and a high risk of lot-to-lot variability. This unspecific labelling can be circumvented by utilizing protein tag-based enzyme-catalysed conjugation (Falck & Müller, 2018, *Antibodies,* 7 (1), 4.). For instance, a Sortase A-based strategy can be employed. In that strategy, the peptide motif LPXTG, with X being K or E for instance, is fused c-terminally to TGF beta 3 or any TGF beta 3 variant and has the following sequence:

[TGF β3 variant]-LPXTGGG, or specifically for TGF β3 T57K L68H S102E:

(SEQ ID NO: 8)
ALDTNYCFRNLEENCCVRPLYIDFRQDLGWKWVHEPKGYYANFCSGPCP

YLRSADTKHSTVLGLYNTHNPEASASPCCVPQDLEPLTILYYVGRTPKV

EQLENMVVKSCKCSLPXTGGG

This fusion protein can be produced recombinantly and purified. Protein stability can be enhanced by a glycopolymer, for instance a polyvinyl made from of 4,6-O-(4-vinylbenzylidene)-α, α-D-trehalose monomers with preferably 18 or more monomers contributing to the polymer. In one synthesis strategy, one glycopolymer terminus is chemically coupled to a GGG peptide, for instance by chemically functionalizing the polymer terminus with an amino group and formation of an amide bond with the carboxy terminus of the C-terminal glycine. This fusion construct GGG-glycopolymer can be enzymatically conjugated via a covalent bonding to a LPXTG motif of the recombinant TGF beta 3 or TGF beta 3 variant by Sortase A in a site-specific (LPXTG-specific) manner.

This results in the following fusion molecule:

[TGF beta 3 variant]-LPXTGGG-glycopolymer, or specifically for TGF beta 3 T57K L68H S102E:

(SEQ ID NO: 9)
ALDTNYCFRNLEENCCVRPLYIDFRQDLGWKWVHEPKGYYANFCSGPCP

YLRSADTKHSTVLGLYNTHNPEASASPCCVPQDLEPLTILYYVGRTPKV

EQLENMVVKSCKCSLPXTGGG-Z3 wherein X is K or E, and $Z^3$ is a glycopolymer, such as a trehalose oligomer, attached to the C-terminus.

In the specific case of a polyvinyl glycopolymer made from n monomers of 4,6-O-(4-vinylbenzylidene)-α,α-D-trehalose for TGF beta 3 T57K L68H S102E the sequence is as follows:

(SEQ ID NO: 18)
ALDTNYCFRNLEENCCVRPLYIDFRQDLGWKWVHEPKGYYANFCSGPCP

YLRSADTKHSTVLGLYNTHNPEASASPCCVPQDLEPLTILYYVGRTPKV

EQLENMVVKSCKCSLPXTGGG- [4,6-O-(4-vinylbenzylidene)-α,α-D-trehalose] n.

Moreover, It is also possible to generate a glycopolymer as a (poly-) peptide by solid-phase peptide synthesis from amino acid monomers conjugated to trehalose moieties (De Bona et al., 2009, *Journal of Peptide Science,* 15 (3), 220-228.). Solid phase peptide synthesis (SPPS) can be controlled in a stepwise manner of amino acid extension. This provides for much more control over the final product length than chemical polymerization as exemplified by the polymerization of 4,6-O-(4-vinylbenzylidene)-α, α-D-trehalose. As a result, product heterogeneity is much smaller in the SPPS-based strategy than in the chemical polymerization-based strategy. To implement such an SPPS-based strategy, a SPPS-compatible (e.g. fmoc/Boc-protected) trehalose-conjugated amino acid must be utilized. One skilled in the art will realize that there are many ways to generate such a reagent. One possibility is to covalently bond amino-functionalized trehalose to side chain carboxyl functions of fmoc-protected amino acid via chemical amidation. More specifically, 6-amino 6-deoxy trehalose (Dutta et al., 2019, ACS Central Science, acscentsci.8b00962) can be used to specifically amidate the gamma carboxyl function of alpha carboxy-protected alpha amino-protected glutamic acid. The resulting 6-deoxy trehalose-functionalized amide, a glutamine-derivative, (Q-6doTh) moiety can be used as building block for SPPS. This may require removal of its alpha carboxy protection group but retention of its alpha amino protection group, which can be achieved by chemical means. As a result a GGG-(Q-6doTh) n polypeptide can be produced, wherein three N-terminal glycine residues are covalently bound to n units of 6-deoxy-trehalose-functionalized glutamines. SPPS enables great control over the number n of these 6-deoxy-trehalose-functionalized glutamines. For stabilization of TGF beta 3 derivatives a number n of 18 or greater is desirable. This trehalose-functionalized peptide can be covalently attached to a TGF beta 3 variant- LPXTG fusion by Sortase A. Such a TGF beta 3 variant-LPXTG fusion protein can be produced recombinantly and purified.

The aforementioned Sortase-mediated conjugation results in the following fusion molecule:

[TGF beta 3 variant]-LPXTGGG-[Q-6doTh]$_n$, or specifically for TGF beta 3 T57K L68H S102E:

(SEQ ID NO: 19)
ALDTNYCFRNLEENCCVRPLYIDFRQDLGWKWVHEPKGYYANFCSGPCP
YLRSADTKHSTVLGLYNTHNPEASASPCCVPQDLEPLTILYYVGRTPKV
EQLENMVVKSCKCSLPXTGGG-[Q-6doTh]$_n$, wherein n is an integer between 15 and 50.

TGF beta 3 variants conjugated to the aforementioned structures containing preferably 18 or more Trehalose variant moieties are stable, e.g. unfolding-resistant and aggregation-resistant, for at least 6 months at 30° C. in standard cosmetic formulations including emulsions. In this context, unfolding-resistance is defined as >95% retention of the folded state as measured by circular dichroism (CD) spectroscopy. Aggregation-resistance is defined as low (<1%) relative abundance of oligomeric species with >4-fold the molecular weight of the monomer or more as measured by dynamic light scattering (DLS). To perform CD spectroscopy and DLS measurements on the purified protein, TGF beta 3 variants were extracted from cosmetic formulations by extensive flow chamber dialysis. Dialysis membrane pores were large enough to permit TGF beta 3 variant membrane trans-permeation. TGF beta 3 variant proteins were simultaneously concentrated from the dilute solution by affinity chromatography.

Preferred concentrations of such stabilized TGF beta 3 variants conjugates in a final cosmetic product range from 80 μM to 500 nM.

Stem Cell Homeostasis Module

Stem cells are key mediators of tissue development, homeostasis, renewal and regeneration upon insult. In turn, they are regulated by various external factors including signalling molecules, cells contacts and the extracellular matrix. One pivotal stem cell regulator in various tissues including the skin is Wnt signalling (Clevers, Loh, & Nusse, 2014, *Science,* 346 (6205), 1248012). Wnt signalling acts on various stem cell populations in distinct niches, e.g. IFE stem cells and HF stem cells, with partly distinct roles (Choi et al., 2013, *Cell Stem Cell,* 13 (6), 720-733). Moreover, it is crucial for homeostatic proliferation of stem cells but can be bypassed by other hyperproliferation-inducing agents during inflammation. Nevertheless, Wnt signalling generally promotes expansion of the stem cell and progenitor compartment. For instance, autocrine Wnt signalling stimulates the self-renewal of Axin2-positive basal layer stem cells in the inter-follicular epidermis (Lim et al., 2013, *Science,* 342 (6163), 1226-1230) and the hair follicle bulge (Jaks et al., 2008, *Nature Genetics,* 40 (11), 1291-1299; Lim, Tan, Yu, Lim, & Nusse, 2016, *Proceedings of the National Academy of Sciences of the United States of America,* 113 (11), E1498-505). Moreover, sustained epidermal Wnt signalling can even induce ectopic hair follicles rich in stem cells. Furthermore, epithelial Wnt/β-catenin signalling influences the dermal compartment and promotes reprogramming of the dermis towards a juvenile, neonatal, state (Collins, Kretzschmar, & Watt, 2011, *Development,* 138 (23), 5189-5199; Lichtenberger, Mastrogiannaki, & Watt, 2016, *Nature Communications,* 7, 1-13). Dermal effects are increased fibroblast proliferation, ECM remodelling, maturation and altered adipogenesis. In particular, epidermal Wnt/β-catenin signalling drives the expansion of the 'pro-regeneration' papillary fibroblast lineage (Driskell et al., 2013, *Nature,* 504 (7479), 277-281).

Nevertheless, Wnt signalling is contextual and can aggravate pathological tissue conditions. For instance, Wnt/β-catenin is a major driver of fibrosis in various tissues including skin (Burgy & Königshoff, 2018, *Matrix Biology,* 68-69, 67-80). Constitutive activation of Wnt/β-catenin even suffices to induce fibrosis in various models (Burgy & Königshoff, 2018, *Matrix Biology,* 68-69, 67-80). This has precluded simple external stimulation of Wnt signalling for cosmetic purposes in the past. In particular, fibrosis manifests as dermis-associated perturbation of fibroblast to myofibroblast transition, aberrant ECM deposition and unresolved inflammation. Accordingly, a spatial separation of Wnt pathway stimulation entailing stimulation of Wnt signalling in the epidermis and absence of stimulation in the dermis could attenuate the issue of fibrosis induction. This kind of spatial control can be easily achieved in experimental model system which allow cell type-specific gene expression of a Wnt pathway-stimulating protein (Lichtenberger et al., 2016, ibid). However, this type of modulation by alteration of the host genome is not possible for routine application in medical or cosmetic products. By contrast, pharmacological stimulators of Wnt signalling are available as small molecules. However, their efficient diffusion and bioavailability within the skin upon topical administration does not permit efficient spatial control of activity. Accordingly, current small molecule Wnt stimulators may exert their activity in the epidermis but would also accumulate in the dermis at efficient concentrations and exert their activity there. Use of natural receptor agonists or their derivatives presents an unexplored hypothetical option. However, this is complicated by the complexity of Wnt agonists encompassing 19 human Wnt proteins that cross-act on at least 10 Fzd receptors and Lrp5/6 co-receptors (Janda et al., 2017, *Nature,* 545 (7653), 234-237; Katoh, 2008, *Current Drug Targets,* 9 (7), 565-570; Nusse & Clevers, 2017, *Cell,* 169 (6), 985-999). Moreover, Wnt proteins classically require site-specific palmitoylation for activity, even though this can be avoided in novel artificial fusion-construct surrogate agonists (Janda et al., 2017, ibid).

This invention discloses novel entities that stimulate Wnt/β-catenin signalling and prove useful for cosmetic use. These molecules are characterised by their stability in conventional cosmetic formulations but short-ranged activity in situ, i.e. sufficient availability of the active variant in the epidermis but not the dermis.

These entities include:

(SEQ ID NO: 1)
LNPSECPKTVLGAEYGKTLDASYSTAEAENHVRL (SEQ ID NO: 2)
LNPSECPKTVLGASTSTLDASYSTAEAENHVRL

Furthermore these peptides can be modified on the N-terminus by fusing a carrier molecule Z1, thereby limiting their tissue penetration and basal membrane transpermeation. This permits the topical application of higher concentrations of the molecules without reaching effective concentrations beyond the basal membrane.

(SEQ ID NO: 3)
(Z1)-LNPSECPKTVLGAEYGKTLDASYSTAEAENHVRL (SEQ ID NO: 4)
(Z1))-LNPSECPKTVLGASTSTLDASYSTAEAENHVRL

A carrier of any size reduces the peptide's tissue penetration and basal membrane transpermeation, thereby providing a benefit. One particularly suitable carrier (Z1) is polyethyleneglycol in the range of 8-60 kDa. It can be covalently coupled to the N-terminus of the peptide using NHS-functionalised PEG. Regardless of the carrier type, Wnt-stimulating entities perform are particularly useful if the epidermis transpermeation half-lifes are higher than 740 hours, thereby allowing the application of higher doses of such entity.

The epidermis transpermeation half-life of such entities can be studied by measuring the concentration of such entities in the epidermis and dermis over time in order to generate a concentration time curve. Measurement can be performed by sampling skin punch biopsies over time, separating epidermis and dermis by surgical dissection, homogenizing and lysing the tissue specimens, enriching the entity of interest in the sample by antibody-based affinity enrichment means and subjecting the enriched sample to mass spectrometric analysis for absolute quantification.

Preferred concentrations of such carrier-conjugated Wnt agonists with an epidermis transpermeation half-life higher than 740 hours in a final cosmetic product range from 150 nM to 500 μM.

Matrikine Module

Matrikines are biologically-active naturally-occurring molecules in the skin that result from degradation of the extracellular matrix during tissue remodelling. The role of the extracellular matrix has been extensively studied in wound healing and scarring (Lo, Zimmermann, Nauta, Longaker, & Lorenz, 2012, *Reviews,* 96 (3), 237-247; Marshall et al., 2016, *Advances in Wound Care,* 7 (2), 29-45; Xue & Jackson, 2015, *Advances in Wound Care,* 4 (3), 119-136). Matrikines can be generated by matrix metallo-proteases (MMP) and can likewise regulate various biological processes such as inflammation, immune cell chemotaxis, organ development, wound healing, ECM synthesis and angiogenesis (Bonnans, Chou, & Werb, 2014, *Nature Reviews Molecular Cell Biology,* 15 (12), 786-801; Bunney, P. E., Zink, A. N., Holm, A. A., Billington, C. J., & Kotz, 2017, *Physiology & Behavior,* 176 (205), 139-148). Alongside growth factors and cytokines, matrikines have become a third pillar of active biologics for skin conditioning in cosmetic products (Aldag, Teixeira, & Leventhal, 2016, *Cosmetic and Investigational Dermatology,* 9, 411-419). For instance, commercial matrikines include the peptides GHK, GEKG, KTTKS and acylated versions thereof, which have been shown to stimulate general ECM synthesis or synthesis of particular ECM proteins such as fibronectin or collagen proteins. However, many more matrikines including bigger fragments of various ECM proteins have been described and to some extent also studied in wound healing (Ricard-Blum & Salza, 2014, *Experimental Dermatology,* 23 (7), 457-463). These include fragments from Aggrecan core protein, Proteoglycan link protein, Fibronections, Laminins, Tenascins, Syndecans, Perlecan, Elastin, Tropoelastin and various Collagens including Collagen IV alpha chains, Collagen XIII alpha chains, Collagen XII alpha chains, Collagen XXIII alpha chains, Collagen XIX alpha chains and Collagen XXV alpha chains. Collagen proteins are some of the most abundant ECM proteins and both pivotal regulators and hallmarks of the ECM state in physiological and pathological processes. For instance, both neonatal skin and non-scarring wound healing skin is known to have a high Collagen III to Collagen I abundance ratio, whereas aged skin and skin of scarring wounds is known to have a low Collagen III to Collagen I abundance ratio (Marshall et al., 2016, *Advances in Wound Care,* 7 (2), 29-45). Furthermore, reduced amounts of collagen III have been shown to promote myofibroblast differentiation and fibrosis (Volk, Wang, Mauldin, Liechty, & Adams, 2011, *Cells Tissues Organs,* 194 (1), 25-37). Collagen III can be degraded by matrix metalloproteases 1,2,3,8,10,13, 14, 16 (Sternlicht & Werb, 2001, *Annual Review of Cell and Developmental Biology,* 463-516). Matrix metalloprotease cleavage motifs have been identified for various MMPs and mostly roughly constitute a PXXL, PXXI, PXXV or PXXM motif (Eckhard et al., 2016, *Matrix Biology,* 49 (2016), 37-60).

This invention discloses that the following peptides derived from Collagen type 3 alpha chain 1 (which coincide with MMP-cleavage sites at both termini in the Collagen type 3 alpha chain 1 sequence) have matrikine activity and can be used for skin wound healing and cosmetic applications:

(SEQ ID NO: 11)
LQGLPGTGGPPGENGKPGEPGPKGDAGAPGAPGGKGDAGAPGERGPPG (SEQ ID NO: 12)
VKGESGKPGANGLSGERGPPGPQG

These peptides can be produced by chemical means such as solid state peptide synthesis or by digesting recombinant collagen type 3 alpha 1 protein with matrix metalloproteases. In case of the latter, these particular peptides of interest can be purified from the hydrolysate by means of liquid chromatography or by electrophoresis such as capillary electrophoresis. Nevertheless, the crude hydrolysate can also be used in cosmetic products.

Moreover, the aforementioned peptides can be acylated on the N-terminus to enhance tissue delivery:

(SEQ ID NO: 13)
Acyl-LQGLPGTGGPPGENGKPGEPGPKGDAGAPGAPGGKGDAGAPGER
GPPG (SEQ ID NO: 14)
Acyl-VKGESGKPGANGLSGERGPPGPQG Acyl can refer to any unbranched fatty acid with 5-42 carbon atoms attached to the peptide via an amide bond between the carboxyl function of the fatty acid and the amino function of the peptide N-terminus, for instance an myristoylation of the peptide N-terminus Preferred concentrations of such acylated Collagen type 3 alpha chain 1-derived peptides in a final cosmetic product range from 50 μM to 500 nM.

EPOR-CD131 Heteroreceptor Agonist Module

Agonists of the EPOR/CD131 heterodimeric or heterooligomeric receptor are tissue-protective agents (Leist, 2004, *Science,* 305 (5681), 239-242). This receptor occurs as heterodimer or heterooligomer comprising the erythropoietin (EPO) receptor and the CD131 protein (cluster of differentiation 131, also known under the names of cytokine receptor common subunit beta or the gene name CSF2RB). However, harnessing this potential has turned out to be challenging. The natural receptor agonist, Erythropoietin, has been dropped early on as a therapeutic agent due to its side effects and other issues. Furthermore, EPOR-CD131 agonist peptide-lipid complexes and conjugates have initially presented elegant alternatives when used in conjunction with vasorelaxant agents (Bader, 2017, PCT/EP2017/001289). These agents proved beneficial in cosmetic formulations in the short term but turned out to be harmful during prolonged administration. This can largely be attributed to a chronic overstimulation of regenerative capabilities, thereby leading to exhaustion of these capabilities. On molecular and cellular level, this is associated with partial stem cell exhaustion, epigenetic changes, impaired differentiation of the progenitor cells into mature cells, and shift of stem cells towards a 'regeneration stimulation'-refractory phenotype. As a result, use of these agents must be controlled tightly to avoid harmful secondary effects. However, this is challenging in practice. First, responsiveness to these agents underlies genotypic variability of multiple proteins of effector signalling pathways in the population. Second, contribution to and manifestation of unwanted long-term effects depends upon the pre-existing tissue condition. Third, individual compliance of self-administration/consumption and a potential compensatory reaction to the declining effect presents a major issue. In a product testing study, some testing individuals tried to compensate a decline in product performance by applying more product or at higher application frequency. However, this even aggravated the decline. Eventually, 58.4% of testing individuals who were initially satisfied with the product experienced a decline of beneficial effects at individual time points within 9 months. Moreover 13.3% of testing individuals even reported adverse effects, i.e. apparent worsening of the skin state compared to before starting the trial.

This invention discloses novel triggering agents that act as agonists to the EPOR/CD131 heterodimeric/heterooligomeric receptor and do not elicit the unwanted long-term effects observed in previous triggering agents of the same class. This is based on two improvements over the previous agents.

The first improvement is the incorporation of a fast inactivation mechanism, that quickly inactivates the active agent in situ, i.e. when applied to the skin. This leads to a short spike in trigger agent activity when new product is applied, which immediately decays. This temporal limitation of activity leads to an only mild decrease in immediate performance of the triggering agent, but also to a significant reduction in unwanted long-term effects.

To implement such a degradation mechanism but retain storability of the product, the degradation must commence or accelerate drastically once the agent is applied. Usually the time point of application coincides with the time point of leaving the storage container. This can be harnessed in combination with the difference of physical, chemical or biological conditions between the point of application, e.g. on the skin, compared to the conditions present in the storage container. This can be harnessed according to the following strategy:

This invention discloses a novel EPOR/CD131 receptor agonist that is sensitive to oxidation by environmental oxidation agents including molecular oxygen from the air in a suitable fashion, thereby entailing a suitably fast oxidation-induced inactivation of the compound upon application. Due to lack of oxidation agents in the storage container, oxidation-induced inactivation does not take place in the storage container.

The sequence of this peptide is the following:

(SEQ ID NO: 5)
GGGGETTNMWAREWMGLPCQDQ

This peptide can be acylated at its N-terminus to increase tissue permeability, giving rise to the following structure:

(SEQ ID NO: 6)
Acyl-GGGGETTNMWAREWMGLPCQDQ

Acyl can refer to any unbranched fatty acid with 5-42 carbon atoms attached to the peptide via an amide bond between the carboxyl function of the fatty acid and the amino function of the peptide N-terminus, for instance an myristoylation of the peptide N-terminus. Upon product contact with air oxygen and subsequent exhaustion of antioxidants, the peptide methionines get oxidised to methionine sulfoxide, thereby inactivating the peptide.

The second improvement is the incorporation of an antagonist, which is also subject to an equivalent degradation. Without an antagonist, application of more product entails application of more active agent, thereby eliciting a stronger and longer stimulation. With an antagonist, application of more product entails application of both more active agent (i.e. agonist) and more antagonist at a constant ratio. As a result, the receptor activation and its downstream signalling can be constrained and made less dependent on the amount of applied product. Rather than absolute amount of agonist and antagonist, their receptor affinity and their potential to activate or inhibit the receptor, respectively, govern the total receptor activation strength. Nevertheless, the antagonist needs to be subject to a similar inactivation as the agonist does. If it did not, the antagonist would become dominant upon inactivation of the agonist. This is unwanted, as it would also inhibit basal endogenous signalling. Furthermore, the antagonist would accumulate through repeated product application, thereby increasing the ratio (i.e. imbalance in this case) of active antagonist to agonist even further.

The sequence of a suitable antagonist compound is the following:

(SEQ ID NO: 17)
GGGGETTNMWAHDWMGLPRADQ

This peptide can be acylated at its N-terminus to increase tissue permeability, giving rise to the following structure:

(SEQ ID NO: 10)
Acyl-GGGGETTNMWAHDWMGLPRADQ

Acyl can refer to any unbranched fatty acid with 5-42 carbon atoms attached to the peptide via an amide bond between the carboxyl function of the fatty acid and the amino function of the peptide N-terminus, for instance an myristoylation of the peptide N-terminus.

Preferred concentrations of such EPOR/CD131 agonist and antagonist peptides in a final cosmetic product range from 30 pM to 250 nM.

Limiting Fibrotic ECM Remodelling by CD26/DPP4 Inhibition

The pro-fibrotic EPF lineage is characterised by CD26 expression and inhibition of CD26 can limit scarring upon injury (Rinkevich et al., 2015, *Science,* 348 (6232)). On cellular and molecular level, this is characterised by reduced fibrosis-associated ECM alterations and reduced myofibroblast differentiation. However, as a result of impairing the natural scarring process by CD26 inhibition wounds take longer to close and heal. Previously low-potency CD26 inhibitors such as diprotin A, a slowly hydrolysable substrate for the CD26 protease, have been used (Rinkevich et al., 2015). High potency orally available small molecule CD26/Dpp4 inhibitors exist as gliptins, however gliptins are associated with severe adverse effects (Attaway, Mersfelder, Vaishnav, & Baker, 2014, *Journal of Dermatological Case Reports,* 8 (1), 24-28; Fisman & Tenenbaum, 2015 September 29, *Cardiovascular Diabetology. BioMed Central* Ltd.; Nakatani et al., 2012, *Diabetes Therapy,* 3 (1), 1-5).

This invention discloses novel CD26/Dpp4 inhibitors suitable for cosmetic application. These include:

```
                                        (SEQ ID NO: 15)
EIHQEEPIGGQSGSGG-KPI
```

The dash between G and K denotes an iso-peptide bond between the carboxy function of G and the epsilon amino function of lysine. Accordingly, the lysine has a free alpha-amino function.

Moreover, the peptide can be acylated to enhance tissue delivery:

```
                                        (SEQ ID NO: 16)
EIHQEEPIGGK[acyl]SGSGG-KPI
```

K[acyl] denotes an amide bond between the epsilon amino function of lysine and the carboxy function of a fatty acid. Acyl can refer to any unbranched fatty acid with 5-42 carbon atoms, for instance myristic acid.

Preferred concentrations of such CD26/Dpp4 inhibitor peptides in a final cosmetic product range from 500 nM to 1 mM.

Combining Signalling Modules to a Trigger Factor Complex

Single skin regeneration enhancing modules disclosed by this invention or specific molecules thereof can be used by themselves in cosmetic products with the aim of skin state improvement. Accordingly, these modules can provide a benefit independently of each other. Nevertheless, it is desirable to combine these modules in one product, thereby unlocking synergistic positive effects on the skin state.

Combination of Molecules Disclosed in this Invention with Conventional Cosmetic Ingredients To the cosmetic formulation further adjuvants and additives can be added to broaden or enhance the described effects of the molecules according to the invention. Such agents are, for example: pycnogenol, coenzyme Q10, ginseng extract, quercetin extract, rice bran extract, soy bean extract, algae extract, tannins, tea extract, in particular green tea extract, mustard extract, alkaloid extracts from cayenne pepper, omega-3 and omega-6 fatty acids, peptides, amino acids, vitamins, in particular vitamin E acetate, sphingolipids, ceramides, growth factors, cytokines, matrikines, vasorelaxants Cosmetic Formulation and Molecule Delivery The formulations of this innovation can be combined with any cosmetic formulation, for example with any cream, lotion, serum etc.

Efficacy Test Data

The inventions disclosed herein can be used in cosmetic products.

To assess the efficacy of this invention in a human skin context a one-month controlled cosmetic skin improvement study was conducted.

In this assay the cosmetic facial skin appearance upon application of the cosmetic formulations containing ingredients of this invention was monitored using the commercially available state-of-the-art facial skin imaging and data analysis platform, the Canfield Bio Visia™. This platform provides the possibility of a (i) highly standardized, (ii) highly reproducible, (iii) quantitative, iv) non-invasive, and (vi) subject or tester bias-free skin quality analysis. It records several photos of the face from different angles and records absorption/reflection spectra. Using these data, the platform quantifies several parameters of skin quality, including 'spots', 'wrinkles', 'pores', 'smoothness', 'UV spots', and 'brown spots'. The in-built software standardizes every parameter by comparison to a large database of skin feature norms and returns a percentage value to permit inter-subject comparison. Healthy subjects received standard cosmetic base formulations with or without trigger factor complexes in a blinded manner, i.e. the subjects were unaware of the identity of the received cosmetic cream. The cosmetic base formulations contained water, caprylic triglyceride, pentylene glycol, propylene glycol, hydrogenated phosphatidylcholine, ceramides, tocopheryl acetate, sodium ascorbate, vasorelaxants, matrikines, amino acids, ethanol and glycerine. Subjects were instructed to apply the cream twice a day and on how much to apply. Subject skin quality was assessed before the start of the application and after one month (30±3 days). As a control, to account for seasonal and lifestyle change-associated skin quality changes, quality of the hand exterior surface was monitored as well. Exterior hand surface skin quality did not change statistically significantly in any subject included in the analysis, thereby indicating that the assay timeline did not correlate with any lifestyle or season-related change in overall skin quality. This study lead to the results described in the section 'Data 1: short-term study. Furthermore, the long-term effects of cosmetic products containing the trigger factor complexes on the facial skin were studied in two long-term nine-month studies wherein product dosage and application frequency were freely chosen by testing subjects to reflect commercial reality. The cosmetic base formulations were identical to the ones used in the one-month study. Participants of the study reported subjective impressions of state of their skin, the effect of the products, and side effects at any time point during the study in regular intervals and when noticing a change. In particular, the participants reported their impressions on how the performance of cosmetic products remained unchanged or changed over the course of the study. The two studies differed in the exact trigger factor complexes used which is detailed together with the study results in the sections 'Data 2: long-term study 1' and 'Data 3: long-term study 2' below.

EXAMPLES

Cosmetic performance information for 4 trigger factor complexes (TFC8-A, TFC8-B, TFC8-C, TFC8-D) obtained in the controlled one-month study is disclosed. Molecules included in these trigger factor complexes are listed in Tables 1-4. TFC8-A and TFC8-C only differ in the molecule of the stem cell homeostasis module. Likewise, TFC8-B and TFC8-D only differ in the molecule of the stem cell homeostasis module.

Example 1: The following trigger factor complex 1 (TFC8-A) was composed:

| | TFC8-A |
|---|---|
| TGF beta 3 module | [TGF beta 3 T57K L68H S102E]-LPETGGG-glycopolymer, (see SEQ ID NO: 18, wherein the glycopolymer is a polyvinyl made from 18 units of 4,6-O-(4-vinylbenzylidene)-α,α-D-trehalose and X in LPXTG is E) |
| Stem cell homeostasis module | LNPSECPKTVLGASTSTLDASYSTAEAENHVRL (See SEQ ID NO: 2) |
| EPOR/ CD131 agonist module | Myristoyl-GGGGETTNMWAREWMGLPCQDQ (see SEQ ID NO: 6, wherein the peptide is myristoylated on the N-terminus and acts as agonist),and Myristoyl-GGGGETTNMWAHDWMGLPRADQ, (see SEQ ID NO: 10, wherein the peptide is myristoylated on the N-terminus and acts as antagonist) |
| CD26/Dpp4 inhibition module | EIHQEEPIGGQSGSGG-KPI (see SEQ ID NO: 15, wherein the dash denotes an isopeptide bond to the epsilon amino group of lysine) |
| Matrikine module | LQGLPGTGGPPGENGKPGEPGPKGDAGAPGAPGGKGDAGAPGERGPPG (see SEQ ID NO: 11), and VKGESGKPGANGLSGERGPPGPQG (see SEQ ID NO: 12) |

Example 2: The following trigger factor complex 2 (TFC8-B) was composed:

| | TFC8-B |
|---|---|
| TGF beta 3 module | [TGF beta 3 T57K L68H S102E]-LPETGGG-$(Q\text{-}6doTh)_{18}$ (see SEQ ID NO: 19, wherein $(Q\text{-}6doTh)_{18}$ denotes a sequence of 18 6-deoxy trehalose-functionalized glutamines and X in LPXTG is E) |
| Stem cell homeostasis module | Z1-LNPSECPKTVLGASTSTLDASYSTAEAENHVRL (see SEQ ID NO: 4, wherein Z1 denotes a polyethylenglycol with a molecular weight of 35 kDa covalently coupled to the peptide N-terminus) |
| EPOR/ CD131 agonist module | Myristoyl-GGGGETTNMWAREWMGLPCQDQ (see SEQ ID NO: 6, wherein the peptide is myristoylated on the N-terminus and acts as agonist), and Myristoyl-GGGGETTNMWAHDWMGLPRADQ (see SEQ ID NO: 10, wherein the peptide is myristoylated on the N-terminus and acts as antagonist) |
| CD26/Dpp4 inhibition module | EIHQEEPIGGK[Myristoyl]SGSGG-KPI (see SEQ ID NO: 16, wherein the dash denotes an isopeptide bond to the epsilon amino group of lysine. K[Myristoyl] denotes an myristoylation at the epsilon amino group of lysine) |
| Matrikine module | Myristoyl-LQGLPGTGGPPGENGKPGEPGPKGDAGAPGAPGG-KGDAGAPGERGPPG (see SEQ ID NO: 13, wherein the peptide is myristoylated on the N-terminus) and Myristoyl-VKGESGKPGANGLSGERGPPGPQG (see SEQ ID NO: 14, wherein the peptide is myristoylated on the N-terminus) |

Example 3: The following trigger factor complex 3 (TFC 8C) was composed:

| | TFC8-C |
|---|---|
| TGF beta 3 module | [TGF beta 3 T57K L68H S102E]-LPETGGG-glycopolymer, (see SEQ ID NO: 18, wherein the glycopolymer is a polyvinyl made from 18 units of 4,6-O-(4-vinylbenzylidene)-α,α-D-trehalose and X in LPXTG is E) |
| Stem cell homeostasis module | LNPSECPKTVLGAEYGKTLDASYSTAEAENHVRL (see SEQ ID NO: 1) |
| EPOR/ CD131 agonist module | Myristoyl-GGGGETTNMWAREWMGLPCQDQ (see SEQ ID NO: 6, wherein the peptide is myristoylated on the N-terminus and acts as agonist),and Myristoyl-GGGGETTNMWAHDWMGLPRADQ |

-continued

| | TFC8-C |
|---|---|
| | (see SEQ ID NO: 10, wherein the peptide is myristoylated on the N-terminus and acts as antagonist) |
| CD26/Dpp4 inhibition module | EIHQEEPIGGQSGSGG-KPI (see SEQ ID NO: 15, wherein the dash denotes an isopeptide bond to the epsilon amino group of lysine) |
| Matrikine module | LQGLPGTGGPPGENGKPGEPGPKGDAGAPGAPGGKGDAGAPGERGPPG (see SEQ ID NO: 11) and VKGESGKPGANGLSGERGPPGPQG (see SEQ ID NO: 12) |

Example 4: The following trigger factor complex 4 (TFC 8D) was composed:

| | TFC8-D |
|---|---|
| TGF beta 3 module | [TGF beta 3 T57K L68H S102E]-LPETGGG-(Q-6doTh)$_{18}$ (see SEQ ID NO: 19, wherein -(Q-6doTh)$_{18}$ denotes a sequence of 18 6-deoxy trehalose-functionalized glutamines and X in LPXTG is E) |
| Stem cell homeostasis module | Z1-LNPSECPKTVLGAEYGKTLDASYSTAEAENHVRL (see SEQ ID NO: 3, wherein Z1 denotes a polyethylenglycol with a molecular weight of 35 kDa covalently coupled to the peptide N-terminus) |
| EPOR/ CD131 agonist module | Myristoyl-GGGGETTNMWAREWMGLPCQDQ (see SEQ ID NO: 6, wherein the peptide is myristoylated on the N-terminus and acts as agonist), and Myristoyl-GGGGETTNMWAHDWMGLPRADQ (see SEQ ID NO: 10, wherein the peptide is myristoylated on the N-terminus and acts as antagonist) |
| CD26/Dpp4 inhibition module | EIHQEEPIGGK[Myristoyl]SGSGG-KPI (see SEQ ID NO: 16, wherein the dash denotes an isopeptide bond to the epsilon amino group of lysine. K[Myristoyl] denotes an myristoylation at the epsilon amino group of lysine) |
| Matrikine module | Myristoyl-LQGLPGTGGPPGENGKPGEPGPKGDAGAPGAPGG-KGDAGAPGERGPPG (see SEQ ID NO: 13, wherein the peptide is myristoylated on the N-terminus), and Myristoyl-VKGESGKPGANGLSGERGPPGPQG (see SEQ ID NO: 14, wherein the peptide is myristoylated on the N-terminus) |

Study Results (as Specified in FIGS. 1 and 2):

Short-Term Study (FIG. 1)

The trigger factor complexes TFC8-A, TFC8-B, TFC8-C, and TFC8-D as specified above were applied in a controlled one-month cosmetic product administration study. The conditions and implementation are described in the section 'Efficacy test data' above.

The results of that controlled one month study are shown in FIG. 1 which depicts the percentage change of normalized "Visia™" facial skin imaging and data analysis platform score (y-axis) in relation to seven types of skin appearances (x-axis), which are here: spots (1), wrinkles (2), UV spots (3), brown spots (4), pores (5), red vascularization (6), and smoothness (7). Skin appearances are shown for all four trigger complexes as specified (the "Visia™" facial skin imaging and data analysis platform score test is described above, in the section Efficacy Test Data). Changes relate to the normalized difference of values (normalized value after 1 month of application-normalized value before start of application). Bars depict mean normalized changes, error bars depict standard deviations. All changes are statistically significantly (p-value<5%) different from 0. Moreover, all changes are statistically significantly (p-value<5%) different from changes observed in subjects that received the vehicle control cosmetic base formulation without any trigger factor complex.

All cosmetic formulations containing trigger factor complexes lead to an improvement in skin appearance as measured by skin parameters reported by the Canfield Bio Visia™ device (facial skin imaging and data analysis platform) over a trial period of 30±3 days.

Long-Term Studies

Study 1: The trigger factor complexes TFC8-A, TFC8-B, TFC8-C, and TFC8-D as specified above in the 'Examples' section were also applied in a nine-month cosmetic product administration study. The conditions and implementation are described in the section 'Efficacy test data' above. Said trigger factor complexes also performed well in the first nine-month long-term administration study with product dosage and application frequency freely chosen by testing subjects indicating broad customer product applicability. All four trigger factor complexes were associated with low risks of stem cell regeneration overstimulation and subsequent exhaustion. Overall, only 7.2% of testing subjects reported a decline of product performance and only 1.6% of testing subjects reported an apparent worsening of the subjectively perceived skin state within the testing period. No significant adverse effects were reported.

Figure 2:
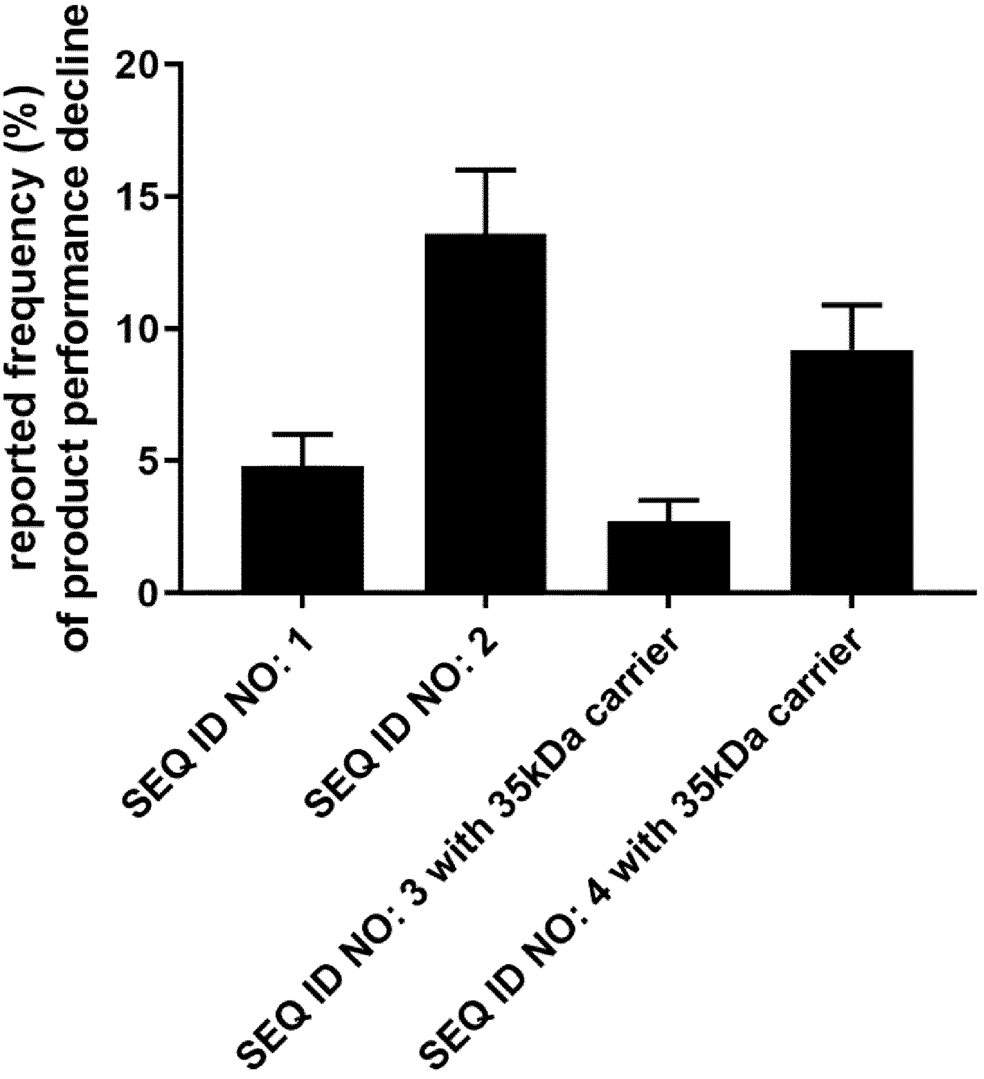

Study 2 (FIG. 2): To further investigate the role of the molecules of the stem cell homeostasis module of the trigger factor complex on the effect of long-term product administration on the skin state, another nine-month long-term study was conducted. The conditions and implementation are described in the section 'Efficacy test data' above. To ensure comparability and specifically investigate the four peptides of the stem cell homeostasis module (SEQ ID NO: 1, SEQ ID NO: 2, SEQ ID NO: 3, SEQ ID NO: 4), these four peptides were tested in conjunction with the same set of molecules of the other modules as specified by the trigger factor complex TFC8-D above in the 'Examples' section. As before, the carrier in the peptide derivatives SEQ ID NO: 3 and SEQ ID NO: 4 was a polyethyleneglycol with a molecular weight of 35 kDa. This second long-term study revealed that the stem cell homeostasis module molecules were differentially associated with the decline of product performance over the course of the study. The frequency of reported product performance decline associated for each of the four peptides are shown in FIG. 2. Error bars represent the 95% confidence intervals of the observed frequency. Overall, the amino acid sequence of SEQ ID NO: 2, contained also in SEQ ID NO: 4, was more strongly associated with a decline in product performance during the study period than the sequence of SEQ ID NO: 1, contained also in SEQ ID NO: 3. These differences were statistically significant (p-value<5%). Secondly, the polyethyleneglycol carrier moderately reduced the frequency of product performance decline in case of both amino acid sequences. Accordingly, the frequency was lower for SEQ ID NO: 3 than for SEQ ID NO: 1 and lower for SEQ ID NO: 4 than for SEQ ID NO: 2.

The invention claimed is:

1. A cosmetic formulation for topical administration to the skin that enhances or improves regeneration or appearance of skin in a form of a cream, a lotion, or a serum, wherein the formulation comprises:

(i) a peptide or a peptide fusion molecule of a first biologically effective group (A) that is provided to stimulate the Wnt/β-catenin signaling pathway in said cosmetic formulation, and elicits short-range activity in situ in the epidermis but not in the dermis, and has the sequences or formula as set forth in:

```
SEQ ID NO: 2:
LNPSECPKTVLGASTSTLDASYSTAEAENHVRL, or

SEQ ID NO: 4:
Z1-LNPSECPKTVLGASTSTLDASYSTAEAENHVRL, or

SEQ ID NO: 1:
LNPSECPKTVLGAEYGKTLDASYSTAEAENHVRL, or

SEQ ID NO: 3:
Z1-LNPSECPKTVLGAEYGKILDASYSTAEAENHVRL,
```

wherein Z1 is a polyethylene glycol (PEG) having a molecular weight in a range 8-60 kDa that is covalently attached to the N-terminus of said peptide, and reduces tissue penetration and/or basal membrane transpermeation of said peptide, (ii) a first peptide fusion molecule of a second biologically effective group (B) that is provided to act as an agonist of the tissue-protective heterodimeric or heterooligomeric EPOR/CD131 (erythropoietin receptor/cluster of differentiation 131) receptor in said cosmetic formulation, having the sequence or formula as set forth in:

```
SEQ ID NO: 6:
Z2-GGGGETTNMWAREWMGLPCQDQ,
```

a second peptide fusion molecule of said second biologically effective group (B) that is provided to act as an antagonist of said receptor in said cosmetic formulation having the sequence or formula as set forth in:

```
SEQ ID NO: 10:
Z2-GGGGETTNMWAHDWMGLPRADQ,
```

wherein Z2 an acyl group of an unbranched or branched fatty acid of 5-42 carbon atoms, attached to the N-terminus of the peptides, and (iii) a peptide fusion molecule of a third biologically effective group (C) that is a variant of human transforming growth factor beta-3 (TGF-β3) and is provided to support healthy skin in said cosmetic formulation, and has the sequences or formula as set forth in

```
SEQ ID NO: 9:
ALDTNYCFRNLEENCCVRPLYIDFRQDLGWKWVHEPKGYYANF-

CSGPCPYLRSADTKHSTVLGLYNTHNPEASASPCCVPQDLE-

PLTILYYVGRTPKVEQLENMVVKSCKCSLPXTGGG-Z3,
```

wherein X is E, and $Z^3$ is an oligomer consisting of 15-50moieties of trehalose or trehalose derivatives.

2. The cosmetic formulation of claim 1, further comprising (iv) a peptide that is provided to elicit CD26/Dpp4 inhibition in said cosmetic formulation and has the sequence or formula as set forth in

```
SEQ ID NO: 15:
EIHQEEPIGGQSGSGG-KPI, or

SEQ ID NO: 16:
EIHQEEPIGGK[Z2]SGSGG-KPI
```

wherein G-K denotes an iso-peptide bond between the carboxy function of G and the epsilon amino function of K, wherein K[Z2] denotes an amide bond between the epsilon amino function of K and the carboxy function of the fatty acid of Z2, and (v) two peptides that are provided to elicit collagen type 3-derived matrikine activity in said cosmetic formulation having the sequences or formulas as set forth in:

```
SEQ ID NO: 11:
LQGLPGTGGPPGENGKPGEPGPKGDAGAPGAPGGKGDAGAP-
GERGPPG, and

SEQ ID NO: 12:
VKGESGKPGANGLSGERGPPGPQG, or

SEQ ID NO: 13:
Z2-LQGLPGTGGPPGENGKPGEPGPKGDAGAPGAP-
GGKGDAGAPGERGPPG, and

SEQ ID NO: 14:
Z2-VKGESGKPGANGLSGERGPPGPQG,
```

wherein Z2 is myristoyl attached to the N-terminus of the peptides.

3. The cosmetic formulation of claim 1, wherein Z3 of SEQ ID NO: 9 is [4,6-O-(4-vinylbenzylidene)-α, α-D-trehalose]$_{18}$, or [Q-6-deoxy-trehalose]$_{18}$.

4. The cosmetic formulation of claim 1, wherein the formulation is designated as "TFC8-A" and comprises:

(i) a peptide fusion molecule that is a variant of human transforming growth factor beta-3 (TGF-β3), and has the sequences or formula as set forth in:

```
SEQ ID NO: 18:
ALDTNYCFRNLEENCCVRPLYIDFRQDLGWKWVHEPKGYYANF-

CSGPCPYLRSADTKHSTVLGLYNTHNPEASASPCCVPQDLE-

PLTILYYVGRTPKVEQLENMVVKSCKCSLPXTGGG-

[4,6-O-(4-vinylbenzylidene)-α,α-D-

trehalose ]18,
```

wherein X is E, (ii) a peptide that is provided to stimulate the Wnt/β-catenin signaling pathway in said cosmetic formulation, and has the sequences or formula as set forth in:

SEQ ID NO: 2: LNP SECPKTVLGASTSTLDASYSTAEAENHVRL, (iii) a first peptide fusion molecule that is provided to act as an agonist of the tissue-protective heterodimeric or heterooligomeric EPOR/CD131 (erythropoietin receptor/cluster of differentiation 131) receptor in said cosmetic formulation, having the sequence or formula as set forth in:

SEQ ID NO: 6:
Z2-GGGGETTNMWAREWMGLPCQDQ, a second peptide fusion molecule that is provided to act as an antagonist of said receptor in said cosmetic formulation having the sequence or formula as set forth in:

SEQ ID NO: 10:
Z2-GGGGETTNMWAHDWMGLPRADQ, wherein Z2 is myristoyl attached to the N-terminus of the peptides, (iv) a peptide that is provided to elicit CD26/Dpp4 inhibition in said cosmetic formulation and has the sequence or formula as set forth in:

SEQ ID NO: 15
EIHQEEPIGGQSGSGG-KPI, wherein G-K denotes an isopeptide bond between the carboxy function of G and the epsilon amino function of K, and (v) two peptides that are provided to elicit collagen type 3-derived matrikine activity in said cosmetic formulation having the sequences or formulas as set forth in:

SEQ ID NO: 11:
LQGLPGTGGPPGENGKPGEPGPKGDAGAPGAPGGKGDAGAP-GERGPPG, and

SEQ ID NO: 12:
VKGESGKPGANGLSGERGPPGPQG.

5. The cosmetic formulation of claim 1, wherein the formulation is designated as "TFC8-β" and comprises:

(i) a peptide fusion molecule that is a variant of human transforming growth factor beta-3 (TGF-β3), and has the sequences or formula as set forth in:

SEQ ID NO: 19:
ALDTNYCFRNLEENCCVRPLYIDFRQDLGWKWVHEPKGYYANF-

CSGPCPYLRSADTKHSTVLGLYNTHNPEASASPCCVPQDLE-

PLTILYYVGRTPKVEQLENMVVKSCKCSLPXTGGG-

[Q-6-deoxy-trehalose]$_{18}$, wherein X is E, (ii) a peptide that is provided to stimulate the Wnt/β-catenin signaling pathway in said cosmetic formulation, and has the sequences or formula as set forth in:

SEQ ID NO: 4:
Z1-LNPSECPKTVLGASTSTLDASYSTAEAENHVRL, wherein Z1 is a 35 kDa polyethylene glycol (PEG) coupled to the N-terminus (iii) a first peptide fusion molecule that is provided to act as an agonist of the tissue-protective heterodimeric or heterooligomeric EPOR/CD131 (erythropoietin receptor/cluster of differentiation 131) receptor in said cosmetic formulation, the peptide fusion molecules having the sequence or formula as set forth in:

SEQ ID NO: 6:
Z2-GGGGETTNMWAREWMGLPCQDQ, a second peptide fusion molecule that is provided to act as an antagonist of said receptor in said cosmetic formulation having the sequence or formula as set forth in:

SEQ ID NO: 10:
Z2-GGGGETTNMWAHDWMGLPRADQ, wherein Z2 is myristoyl attached to the N-terminus of the peptides (iv) a peptide that is provided to elicit CD26/Dpp4 inhibition in said cosmetic formulation and has the sequence or formula as set forth in:

SEQ ID NO: 16:
EIHQEEPIGGK[Z2]SGSGG-KPI wherein G-K denotes an isopeptide bond between the carboxy function of G and the epsilon amino function of K, and $Z^2$ is myristoyl attached to the epsilon amino function of K, and K[Z2] denotes an amide bond between the epsilon amino function of K and the carboxy function of Z2, and (v) two peptides that are provided to elicit collagen type 3-derived matrikine activity in said cosmetic formulation having the sequences or formulas as set forth in:

SEQ ID NO: 13:
Z2-LQGLPGTGGPPGENGKPGEPGPKGDAGAPGAPGGKGDA-GAPGERGPPG, and

SEQ ID NO: 14:
Z2-VKGESGKPGANGLSGERGPPGPQG wherein Z2 is myristoyl attached to the N-terminus of the peptides.

6. The cosmetic formulation of claim 1, wherein the formulation is designated as "TFC8-C" and comprises:

(i) a peptide fusion molecule that is a variant of human transforming growth factor beta-3 (TGF-β3), and has the sequences or formula as set forth in:

SEQ ID NO: 18:
ALDTNYCFRNLEENCCVRPLYIDFRQDLGWKWVHEPKGYYANF-

CSGPCPYLRSADTKHSTVLGLYNTHNPEASASPCCVPQDLE-

PLTILYYVGRTPKVEQLENMVVKSCKCSLPXTGGG-

[4,6-O-(4-vinylbenzylidene)-

α,α-D-trehalose]$_{18}$, wherein X is E, (ii) a peptide that is provided to stimulate the Wnt/β-catenin signaling pathway in said cosmetic formulation, and has the sequences or formula as set forth in:

SEQ ID NO: 1:
LNPSECPKTVLGAEYGKTLDASYSTAEAENHVRL, (iii) a first peptide fusion molecule that is provided to act as an agonist of the tissue-protective heterodimeric or heterooligomeric EPOR/CD131 (erythropoietin receptor/cluster of differentiation 131) receptor in said cosmetic formulation, the peptide fusion molecules having the sequence or formula as set forth in:

SEQ ID NO: 6:
Z2-GGGGETTNMWAREWMGLPCQDQ, a second peptide fusion molecule that is provided to act as an antagonist of said receptor in said cosmetic formulation having the sequence or formula as set forth in:

SEQ ID NO: 10:
Z2-GGGGETTNMWAHDWMGLPRADQ, wherein Z2 is myristoyl attached to the N-terminus of the peptides (iv) a peptide that is provided to elicit CD26/Dpp4 inhibition in said cosmetic formulation and has the sequence or formula as set forth in:

SEQ ID NO: 15
EIHQEEPIGGQSGSGG-KPI, wherein G-K denotes an isopeptide bond between the carboxy function of G and the epsilon amino function of K, and (v) two peptides that are provided to elicit collagen type 3-derived matrikine activity in said cosmetic formulation having the sequences or formulas as set forth in:

SEQ ID NO: 11:
LQGLPGTGGPPGENGKPGEPGPKGDAGAPGAPGGKGDAGAP-GERGPPG, and

SEQ ID NO: 12:
VKGESGKPGANGLSGERGPPGPQG.

7. The cosmetic formulation of claim 1, wherein the formulation is designated as "TFC8-D" and comprises:

(i) a peptide fusion molecule that is a variant of human transforming growth factor beta-3 (TGF-β3), and has the sequences or formula as set forth in:

SEQ ID NO: 19:
ALDTNYCERNLEENCCVRPLYIDFRQDLGWKWVHEPKGYYANF-

CSGPCPYLRSADTKHSTVLGLYNTHNPEASASPCCVPQDLE-

PLTILYYVGRTPKVEQLENMVVKSCKCSLPXTGGG-

[Q-6-deoxy-trehalose]$_{18}$, wherein X is E, (ii) a peptide that is provided to stimulate the Wnt/β-catenin signaling pathway in said cosmetic formulation, and has the sequences or formula as set forth in:

SEQ ID NO: 3:
Z1-LNPSECPKTVLGAEYGKTLDASYSTAEAENHVRL, wherein Z1 is a 35 kDa polyethylene glycol (PEG) coupled to the N-terminus, (ii) a first peptide fusion molecule that is provided to act as an agonist of the tissue-protective heterodimeric or heterooligomeric EPOR/CD131 (erythropoietin receptor/cluster of differentiation 131) receptor in said cosmetic formulation, the peptide fusion molecules having the sequence or formula as set forth in:

SEQ ID NO: 6:
Z2-GGGGETTNMWAREWMGLPCQDQ, a second peptide fusion molecule that is provided to act as an antagonist of said receptor in said cosmetic formulation having the sequence or formula as set forth in:

SEQ ID NO: 10:
Z2-GGGGETTNMWAHDWMGLPRADQ,, wherein Z2 is myristoyl attached to the N-terminus of the peptides (iv) a peptide that is provided to elicit CD26/Dpp4 inhibition in said cosmetic formulation and have the sequence or formula as set forth in:

SEQ ID NO: 16:
EIHQEEPIGGK[Z2]SGSGG-KPI wherein G-K denotes an isopeptide bond between the carboxy function of G and the epsilon amino function of K, and K[Z2] denotes an amide bond between the epsilon amino function of K and the carboxy function of Z2, and (v) two peptides that are provided to elicit collagen type 3-derived matrikine activity in said cosmetic formulation having the sequences or formulas as set forth in:

SEQ ID NO: 13:
Z2-LQGLPGTGGPPGENGKPGEPGPKGDAGAPGA-PGGKGDAGAP GERGPPG, and

SEQ ID NO: 14:
Z2-VKGESGKPGANGLSGERGPPGPQG wherein Z2 is myristoyl attached to N-terminus of the peptides.

8. The cosmetic formulation or composition according to claim 1, wherein Z1 is a polyethylene glycol having a molecular weight in a range of 20-40 kDa.

9. The cosmetic formulation or composition according to claim 1, wherein Z2 is myristoyl.

10. The cosmetic formulation or composition according to claim 1, further comprising at least one peptide or peptide derivative that elicits collagen type 3-derived matrikine activity and comprising or having one of the sequences/formulas selected from the group consisting of:

SEQ ID NO: 11:
LQGLPGTGGPPGENGKPGEPGPKGDAGAPGAPGGKGDAGAP-GERGPPG,

SEQ ID NO: 12:
VKGESGKPGANGLSGERGPPGPQG,

SEQ ID NO: 13:
Z2-LQGLPGTGGPPGENGKPGEPGPKGDAGAPGAP-GGKGDAGAPGERGPPG, and

SEQ ID NO: 14:
Z2-VKGESGKPGANGLSGERGPPGPQG.

11. The cosmetic formulation or composition according to claim 1, further comprising at least one peptide or peptide derivative that elicits CD26/Dpp4 inhibition and comprises or has one of the sequences/formulas selected from the group consisting of:

```
SEQ ID NO: 15:
EIHQEEPIGGQSGSGG-KPI, and

SEQ ID NO: 16:
EIHQEEPIGGK[Z2]SGSGG-KPI
```

wherein G-K denotes an isopeptide bond between the carboxy function of G and the epsilon amino function of K, and K[Z2] denotes an amide bond between the epsilon amino function of K and the carboxy function of the fatty acid Z2.

12. The cosmetic formulation or composition according to claim 10, wherein Z2 is myristoyl.

13. The cosmetic formulation or composition according to claim 11, wherein Z2 is myristoyl.

* * * * *